United States Patent [19]

Freerksen

[11] Patent Number: 4,500,344
[45] Date of Patent: Feb. 19, 1985

[54] HERBICIDAL ORTHO-(ALKOXY)-BENZENESULFONAMIDES

[75] Inventor: Robert W. Freerksen, Wilmington, Del.

[73] Assignee: E. I. Du Pont de Nemours and Company, Wilmington, Del.

[21] Appl. No.: 474,873

[22] Filed: Mar. 21, 1983

[51] Int. Cl.³ .................. C07D 251/18; C07D 251/46; C07D 251/52; A01N 43/70
[52] U.S. Cl. ........................................ 71/93; 544/211; 544/212; 544/206; 544/207; 544/208; 544/209
[58] Field of Search .............. 544/211, 212, 206, 208, 544/207, 209; 71/93

[56] References Cited

U.S. PATENT DOCUMENTS 4,127,405 11/1978 Levitt ...................................... 71/93
4,169,719 10/1979 Levitt ...................................... 71/92

FOREIGN PATENT DOCUMENTS 830441 7/1983 South Africa .

Primary Examiner—John M. Ford

[57] ABSTRACT

Ortho-(alkoxy)benzenesulfonamides, such as N-[(4-methoxy-6-methyl-1,3,5-triazin-2-yl)aminocarbonyl]-2-(2-hydroxyethoxy)benzenesulfonamide, are useful as pre- and post-emergent herbicides.

24 Claims, No Drawings

HERBICIDAL ORTHO-(ALKOXY)-BENZENESULFONAMIDES

BACKGROUND OF THE INVENTION

This invention relates to benzenesulfonamide compounds and, more particularly, to ortho-(alkoxy)-benzenesulfonamides which are useful as general or selective pre-emergent or post-emergent herbicides.

U.S. Pat. No. 4,169,719 discloses and claims N-(heterocyclicaminocarbonyl)arylsulfonamides of the formula:

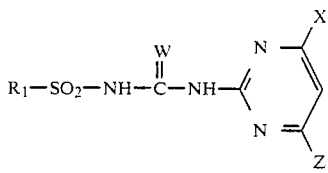

wherein $R_1$ can be

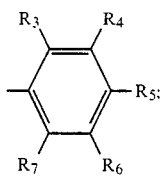

W can be O or S;

$R_3$, $R_4$, $R_5$, $R_6$ and $R_7$ can be H, alkyl, halo or alkoxy, as more specifically defined therein; and X and Z can be various substituents including H, methyl and methoxy.

These compounds are useful as plant growth regulants and as herbicides.

U.S. Pat. No. 4,127,405 also discloses and claims benzenesulfonamides such as, N-(1,3,5-triazin-2-ylaminocarbonyl)arylsulfonamides, which can be used as plant growth regulants and herbicides.

U.S. patent application Ser. No. 06/377,370 filed May 12, 1982, now abandoned, discloses and claims 2-alkoxybenzenesulfonamides of the formula

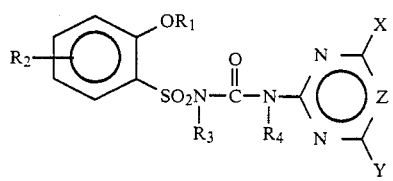

wherein $R_1$ can be $CH_2R_5$, —$CH(CH_3)R_5$, $CH_2CH_2R_6$, $CH(CH_3)CH_2OCH_3$, $CH_2CH(CH_3)OCH_3$ or cyclopentyl;

$R_2$ is H, F, Cl, Br, $CH_3$, $OCH_3$ or $CF_3$;

$R_3$ is H or $CH_3$;

$R_4$ is H or $CH_3$;

$R_5$ can be CN, $CO_2CH_3$, $CO_2C_2H_5$, $S(O)_nCH_3$, $OCH_3$, $OC_2H_5$, $CH=CH_2$, $C\equiv CH$, $SO_2N(CH_3)_2$ or cyclopropyl;

$R_6$ is Cl, Br, $OCH_3$, $OC_2H_5$, $N(CH_3)_2$, CN, $CO_2CH_3$, $CO_2C_2H_5$, $SO_2N(CH_3)_2$ or $S(O)_nCH_3$;

n is 0, 1 or 2;

Z is CH or N;

X is $CH_3$, $OCH_3$ or Cl; and

Y can be $CH_3$, $C_2H_5$, $OCH_3$, $OC_2H_5$, $CH_2OCH_3$, $CH(OCH_3)_2$,

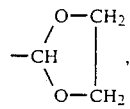

$NH_2$, $NHCH_3$ or $N(CH_3)_2$.

These compounds are also useful as general and selective herbicides.

U.S. application Ser. No. 06/437,631, filed Oct. 29, 1982, now abandoned, relates to herbicidal benzenesulfonamides which possess selective post-emergent activity against undesired vegetation growing in association with corn. These compounds have the following general formula:

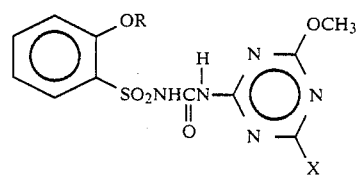

wherein

R is $C_2H_5$, $C_3H_7$, $CH(CH_3)_2$, $CH_2CH_2CH_2CH_3$, $CH(CH_3)CH_2CH_3$ or $CH_2CH(CH_3)_2$; and X is $OCH_3$ or $CH_3$.

SUMMARY OF THE INVENTION

This invention relates to compounds of Formula I, agriculturally suitable compositions containing them and their method-of-use as general or selective pre-emergent or post-emergent herbicides.

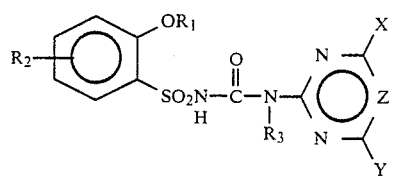

wherein $R_1$ is $\underset{R_5}{\underset{|}{CH}}-\underset{R_6}{\underset{|}{C}}-OR_4$ or $\underset{R_8}{\underset{|}{CH}}-\underset{R_9}{\underset{|}{CH}}-\underset{R_{10}}{\underset{|}{CH}}-OR_4;$ $R_2$ is H, F, Cl, Br, $CH_3$, $OCH_3$ or $CF_3$;

$R_3$ is H or $CH_3$;

$R_4$ is H, $COCH_3$, $COC_2H_5$, $COCH_2CH_2CH_3$, $COCH(CH_3)_2$, $COC_6H_5$, $CONHCH_3$, $CONHC_2H_5$, $CON(CH_3)_2$,

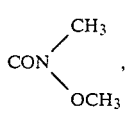

CONHC$_6$H$_5$, SO$_2$CH$_3$, SO$_2$C$_2$H$_5$, SO$_2$C$_6$H$_5$,

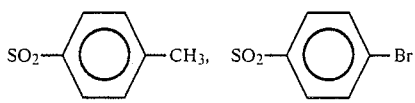

or SO$_2$CF$_3$;
R$_5$ is H or CH$_3$;
R$_6$ is H or CH$_3$;
R$_7$ is H or CH$_3$;
R$_8$ is H or CH$_3$;
R$_9$ is H or CH$_3$;
R$_{10}$ is H or CH$_3$;
Z is CH or N;
X is CH$_3$, OCH$_3$ or Cl; and
Y is CH$_3$, C$_2$H$_5$, OCH$_3$, OC$_2$H$_5$, CH$_2$OCH$_3$, CH(OCH$_3$)$_2$,

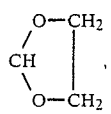

NH$_2$, NHCH$_3$
or N(CH$_3$)$_2$;
provided that
(1) when R$_6$ and R$_7$ are both CH$_3$, then R$_4$ is H;
(2) when either R$_8$, R$_9$ or R$_{10}$ is CH$_3$, then the others must be H; and
(3) when X is Cl, then Y is OCH$_3$, CH$_3$, OC$_2$H$_5$, NH$_2$, NHCH$_3$ or N(CH$_3$)$_2$ and Z is CH;
and their agriculturally suitable salts.

Preferred for their higher herbicidal activity and/or more favorable ease of synthesis are:
(1) Compounds of Formula I where

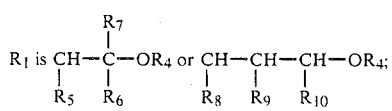

R$_7$ is H;
R$_8$ is H;
R$_9$ is H; and
R$_{10}$ is H.
(2) Compounds of Preferred 1 where R$_3$ is H.
(3) Compounds of Preferred 2 where R$_2$ is H; and R$_4$ is H, COCH$_3$, CONHCH$_3$, SO$_2$CH$_3$ or SO$_2$CF$_3$.
(4) Compounds of Preferred 3 where

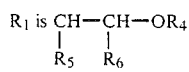

or CH$_2$CH$_2$CH$_2$OR$_4$; R$_4$ is H; R$_5$ is H; and R$_6$ is H.
(5) Compounds of Preferred 4 where X and Y are independently CH$_3$ or OCH$_3$.

Specifically preferred for their highest herbicidal activity and/or most favorable ease of synthesis are:
N-[(4-methoxy-6-methyl-1,3,5-triazin-2-yl)aminocarbonyl]-2-(2-hydroxyethoxy)benzenesulfonamide;
N-[(4,6-dimethoxy-1,3,5-triazin-2-yl)aminocarbonyl]-2-(2-hydroxyethoxy)benzenesulfonamide;
N-[(4,6-dimethoxypyrimidin-2-yl)aminocarbonyl]-2-(2-hydroxyethoxy)benzenesulfonamide;
N-[4-methoxy-6-methylpyrimidin-2-yl)aminocarbonyl]-2-(2-hydroxyethoxy)benzenesulfonamide;
N-[4,6-dimethylpyrimidin-2-yl)aminocarbonyl]-2-(2-hydroxyethoxy)benzenesulfonamide; and
N-[4-methoxy-6-methylpyrimidin-2-yl)aminocarbonyl]-2-(2-methylsulfonyloxyethoxy)benzenesulfonamide.

DETAILED DESCRIPTION OF THE INVENTION

Synthesis

The compounds of Formula (1) can be prepared by one or more of the methods described below in Equations 1 to 4. As shown in Equation 1 below, many of the compounds of Formula (1), wherein R$_1$, R$_2$ and R$_3$ are as previously defined and R$_4$ is not H can be prepared by reacting an appropriately substituted sulfonyl isocyanate of Formula (2) with an appropriate 2-aminopyrimidine, 2-amino-1,3,5-triazine, 2-alkylaminopyrimidine or 2-alkylamino-1,3,5-triazine of Formula (3), wherein X, Y and Z are as previously defined.

Equation 1

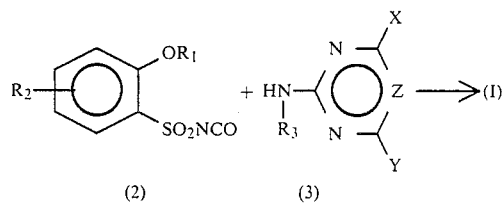

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine (3). Since such isocyanates are usually liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration. The compounds of Formula (1) can be purified by recrystallization or chromatography.

Compounds of Formula (1) wherein R$_4$ is H can be prepared from compounds of Formula (1) wherein R$_4$ is an alkyl or aryl sulfonyl group by contacting the sulfonate ester with dilute aqueous base. In some cases compounds of Formula (1) wherein R$_4$ is H can be prepared directly by reacting compounds of Formula (2) wherein R$_4$ is SO$_2$CH$_3$ with compounds of Formula (3).

Some of the compounds of Formula (1) wherein R$_4$ is not H can best be prepared as shown in Equation 2 below. Reaction of a sulfonamide of Formula (4) with an appropriate methyl pyrimidinyl carbamate or methyl triazinyl carbamate of Formula (5) in the presence of an equimolar amount of trimethylaluminum, leads to compounds of Formula (1) wherein R$_1$, R$_2$, R$_4$, X, Y and Z are as previously defined and R$_3$ is H.

Equation 2

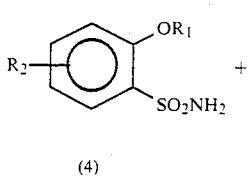

(4)

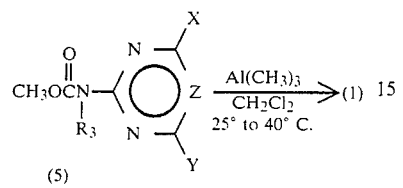

(5)

The reaction of Equation 2 is best run in methylene chloride or dichloroethane at about 25° to the reflux temperature of the solvent for 10 to 96 hours under a nitrogen atmosphere. The product can be isolated by addition of an aqueous acid solution followed by extraction of the product into methylene chloride, or by filtration of a product of low solubility. The product can be purified by trituration with solvents such as 1-chlorobutane, ethyl acetate or ethyl ether or by column chromatography on silica gel.

Compounds of Formula (1) wherein $R_4$ is not H can be prepared from compounds of Formula (1) where $R_4$ is H by treatment with an appropriate acyl halide, sulfonyl halide or carbamoyl halide in the presence of an acid acceptor or, in the case wherein $R_4$ is methylamino carbonyl, ethylamino carbonyl or phenylamino carbonyl, by treatment with the appropriate isocyanate. The reaction is best conducted in an inert solvent such as tetrahydrofuran in the presence of a base such as triethylamine at a temperature of from 0° to 40° for from one hour to several hours. The reaction of acid halides may be accelerated by the addition of a small amount of a catalyst such as 4-dimethylaminopyridine.

Some of the compounds of Formula (1) wherein $R_4$ is H can be prepared by one or both of the processes described by Equation 3 and Equation 4 below, wherein $R_1$, $R_2$, $R_3$, $R_5$, $R_6$, $R_7$, X, Y and Z are as previously defined and Q is a leaving group such as chloro, bromo, iodo or a sulfonate ester.

Equation 3

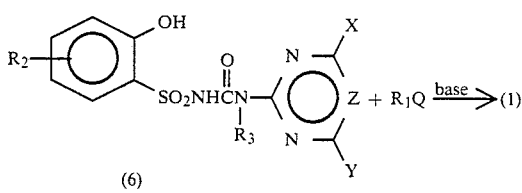

Equation 4

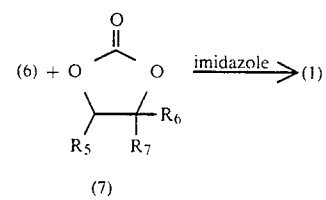

The reaction described by Equation 3 can be carried out in a dipolar aprotic solvent such as dimethylformamide in the presence of a base such as potassium carbonate or potassium bicarbonate. The reaction can be conducted at temperatures ranging from 20° to 100°, for a period of from a few hours to several days. The product is isolated by neutralization of the reaction mixture with dilute aqueous acid and extraction with a solvent such as ethyl acetate. The crude product can be purified by trituration, recrystallization or by chromatography.

The reaction described by Equation 4 is best conducted by mixing the sulfonylurea of Formula (6) with an equimolar amount or an excess of a carbonate ester of Formula (7) in the presence of a catalyst such as imidazole. The reactants are mixed vigorously and heated to a temperature sufficient to cause the liberation of carbon dioxide, with 130° to 160° being preferred. Compounds of Formula (1) are isolated by trituration with a solvent such as diethyl ether, by recrystallization or by chromatography.

The 2-hydroxybenzenesulfonylureas of Formula (6) are themselves prepared from the corresponding 2-benzyloxybenzenesulfonylureas by methods taught in the copending application U.S. Ser. No. 304,301, the disclosures of which are herein incorporated by reference.

Many of the intermediate sulfonyl isocyanates of Formula (2) in Equation 1 above can be prepared from sulfonamides (4) by methods described in U.S. Pat. No. 4,238,621. These methods require reacting sulfonamides with phosgene, in the presence of n-butyl isocyanate and a tertiary amine catalyst, at reflux in a solvent such as xylene. A preferred catalyst is 1,4-diazabicyclo[2.2.2]octane (DABCO).

Alternatively, many of the sulfonyl isocyanates (2) can be prepared from sulfonamides (4) by a two-step procedure. This consists of first reacting the sulfonamide with n-butyl isocyanate and a base such as potassium carbonate at reflux in an inert solvent such as 2-butanone to form a n-butyl sulfonylurea; and secondly reacting this product with phosgene and DABCO catalyst at reflux in xylene solvent. This method is similar to a procedure taught by Ulrich and Sayigh, *Newer Methods of Preparative Organic Chemistry, Vol. VI, p. 223–241*, Academic Press, New York and London, W. Foerst Ed.

Equation 5 shown below illustrates the preparation of the required methyl pyrimidinyl carbamates and methyl triazinyl carbamates of Formula (5) in Equation 2 above, wherein $R_3$, X, Y and Z are as previously defined.

Equation 5

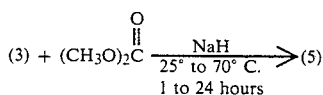

According to Equation 5, a heterocyclic amine of Formula (3) is reacted with two equivalents of sodium hydride and excess dimethylcarbonate to form (5). The reaction is run in an inert solvent such as tetrahydrofuran at 25° C. to reflux for 1 to 24 hours. The product is isolated by (a) adding about two equivalents of concentrated HCl and water saturated with NaCl, and (b) separating out the organic phase and concentrating to dryness in vacuo.

The synthesis of heterocylic amines such as (3) above has been reviewed in "The Chemistry of Heterocyclic Compounds", a series published by Interscience Publ., New York and London. 2-Aminopyrimidines are described by D. J. Brown in "The Pyrimidines", Vol. XVI of this series. 2-Amino-1,3,5-triazines can be prepared according to methods described by E. M. Smolin and L. Rapaport in "s-Triazines and Derivatives", Vol. XIII of the same series. The synthesis of triazines is also described by F. C. Schaefer, U.S. Pat. No. 3,154,547 and by K. R. Huffman and F. C. Schaefer; *J. Org. Chem.*, 28, 1816 (1963).

The preparation of sulfonamides of Formula (4) wherein $R_4$ is H can be accomplished by one or more of the methods described below in Equations 6 to 9, wherein $R_1$, $R_2$, $R_5$, $R_6$, $R_7$, $R_8$, $R_9$, $R_{10}$ and Q are as previously defined.

Equation 6

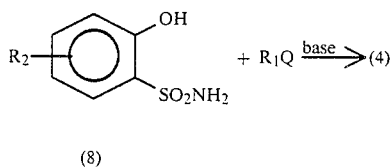

(8)

The reaction described by Equation 6 can be conducted in solvents such as dimethylformamide, dimethyl sulfoxide, acetone or 2-butanone at a temperature of from 25° to the reflux temperature of the solvent for a period of from a few hours to several days. Bases which can be employed include potassium carbonate, potassium bicarbonate and sodium hydride.

Equation 7

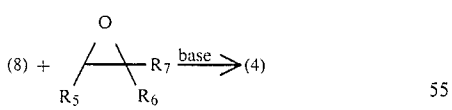

The reaction described by Equation 7 can be conducted in a solvent such as dimethyl sulfoxide or in the absence of a solvent. Bases which may be employed include potassium carbonate, potassium bicarbonate and sodium hydride.

Equation 8

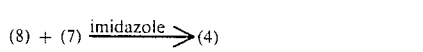

Equation 9

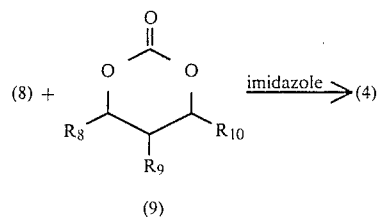

(9)

The reaction described by Equation 8 and Equation 9 are conducted by heating a mixture of one part of the 2-hydroxybenzenesulfonamide of Formula (8), one molar equivalent to several equivalents of an appropriately substituted carbonate ester of Formula (7) or Formula (9) and from one one-hundreth part to one-tenth part of a catalyst such as imidazole. The combined reactants are mixed vigorously in the absence of a solvent and are heated to a temperature at least sufficient to liquefy the mixture and to cause the liberation of carbon dioxide, with a temperature of from 130° to 160° being preferred. Heating is continued until the evolution of carbon dioxide has ceased and the reaction is deemed to be complete by analytical methods such as chromatography. The sulfonamides of Formula (4) are isolated by trituration with a solvent such as diethyl ether and can be purified by recrystallization or by chromatography. Reactions wherein the carbonate esters of Formula (7) or Formula (9) are asymmetrically substituted may result in the formation of regioisomeric product mixtures which may require further separation by methods such as chromatography. The carbonate esters of Formula (7) and Formula (9) are themselves prepared from the corresponding diols and phosgene by methods well known in the art.

The sulfonamides of Formula (4) wherein $R_4$ is not H can be prepared from the appropriate sulfonamide of Formula (4) wherein $R_4$ is H by treatment of the alcohol with the appropriate acyl halide, sulfonyl halide, carbamoyl halide or isocyanate. The reaction is best conducted in an inert solvent such as tetrahydrofuran in the presence of a base such as triethylamine at a temperature of from 0° to 40° for from one hour to several hours. The reaction of acid halides may be accelerated by the addition of a catalyst such as 4-dimethylaminopyridine.

The 2-hydroxybenzenesulfonamides of Formula (8) can be prepared using one or more of the methods described below in Equations 10 to 13.

Equation 10

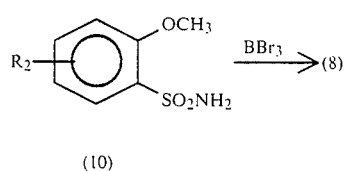

(10)

Equation 11

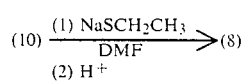

Equation 12

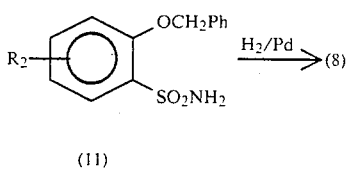

(11)

Equation 13

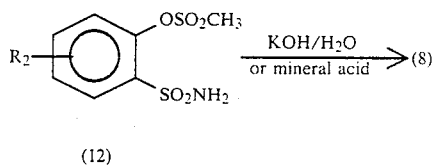

(12)

The methyl aryl ethers of Formula (10) can be cleaved by methods well known in the art. Cleavage with Lewis acids, such as boron tribromide, is shown in Equation 10 and such reactions are described in *J. Am. Chem. Soc.*, 64, 1128 (1942). Equation 11 illustrates cleavage by sulfur nucleophiles and such reactions are described in *Tetrahedron Letters* 1327 (1970). Hydrogenolysis of the benzyloxybenzenesulfonamides of Formula (11) may also be employed for the preparation of the 2-hydroxybenzenesulfonamides (8). Reactions of this type are described in *J. Chem. Soc.*, 2903 (1958). Methanesulfonate esters of Formula (12) are cleaved using aqueous base or mineral acids. The cleavage of methanesulfonate esters and the preparation of 2-sulfamylphenyl sulfonates (12) is described in *Research Disclosure*, pg. 52 (1978).

Agriculturally suitable salts of compounds of Formula (1) are also useful herbicides and can be prepared in a number of ways known in the art. For example, metal salts can be made by contacting compounds of Formula (1) with a solution of an alkali or alkaline earth metal salt having a sufficiently basic anion (e.g., alkoxide, carbonate or hydroxide). Quaternary amine salts can be made by similar techniques.

Salts of compounds of Formula (1) can also be prepared by exchange of one cation for another. Cationic exchange can be effected by direct contact of an aqueous solution of a salt of a compound of Formula (1) (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula (1) (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula (1) with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

2-(2-Hydroxyethoxy)benzenesulfonamide

A mixture of 74.6 g of (0.43 mol) of 2-hydroxybenzenesulfonamide, 45.3 g (0.51 mol) of ethylene carbonate and 0.9 g of imidazole was heated to 160° with vigorous stirring. After about four hours the carbon dioxide solution had subsided and no unreacted 2-hydroxybenzenesulfonamide was present in the reaction mixture. The mixture was allowed to cool and about 400 ml of diethyl ether was added to the thick oil. The two-phase mixture was stirred vigorously and was heated to reflux for about one hour. The diethyl ether was decanted off and a fresh portion of diethyl ether was added. The mixture was again stirred and heated to reflux. After the diethyl ether was decanted off a fresh portion of diethyl ether was added and the mixture was allowed to stand at ambient temperature for about 18 hours. The resulting light brown solid was isolated by filtration and was recrystallized from nitromethane to afford 49 g (53%) of trum exhibited a broad peak at approximately 3400 cm$^{-1}$ consistent with the primary alcohol of the product and peaks at 3370 cm$^{-1}$ and 3270 cm$^{-1}$ consistent with the NH$_2$ of a primary sulfonamide.

NMR (DMSO-d$_6$): δ3.7–3.95 (m, 2, —C$\underline{H}_2$OH); 4.05–4.3 (m, 2, ArOC$\underline{H}_2$—); 6.3–7.05 (broad s, 2, NH$_2$); and 7.05–7.9 (m, 4, aromatic H).

EXAMPLE 2

2-(2-Hydroxyethoxy)benzenesulfonamide, Methanesulfonate ester

A mixture of 24.5 g (0.113 mol) of 2-(2-hydroxyethoxy)benzenesulfonamide and about 0.1 g of 4-dimethylaminopyridine was dissolved in 200 ml of dry tetrahydrofuran. The solution was cooled to 4° under a calcium sulfate drying tube and 9.6 ml (14.2 g, 0.124 mol) of methanesulfonyl chloride was added. The slow addition of 24 ml (17.1 g, 0.169 mol) of triethylamine was then begun. The rate of addition was controlled such that the reaction temperature was maintained between 0° and 10°. After the addition was complete the mixture was allowed to warm to ambient temperature and stirred for 3 hours. The reaction mixture was then poured into a mixture of 500 ml of 5% hydrochloric acid and about 1000 g of ice. The solid product was collected by filtration, washed with water and then washed with a small amount of diethyl ether. After the product had dried it was recrystallized from 2-propanol to afford 15.3 g (46%) of the title compound; m.p. 120°–125° C. The infrared spectrum exhibited peaks at 3290 cm$^{-1}$ and 3270 cm$^{-1}$ consistent with the NH$_2$ of a primary sulfonamide and peaks at 1345 cm$^{-1}$, 1325 cm$^{-1}$, 1175 cm$^{-1}$ and 1160 cm$^{-1}$ consistent with the SO$_2$ groups of a sulfonamide and a sulfonate ester.

NMR (DMSO-d$_6$): δ3.25 (s, 3, OSO$_2$CH$_3$); 4.3–4.8 (m, 4, OCH$_2$CH$_2$O); 7.0 (broad s, 2, NH$_2$); and 7.15–8.0 (m, 4, aromatic H).

EXAMPLE 3

N-[(4-Methoxy-6-methylpyrimidin-2-yl)aminocarbonyl]-2-(2-methylsulfonyloxyethoxy)benzenesulfonamide To 1.5 g (0.01 mol) of 2-(2-hydroxyethoxy)benzenesulfonamide methanesulfonate ester suspended in 100 ml of dry dichloromethane under a nitrogen atmosphere was added dropwise 3.0 ml (0.012 mol) of a 2M solution of trimethylaluminum in toluene. Gas evolution and a mild exotherm occured during the addition of the trimethylaluminum solution and the mixture slowly became homogeneous. After stirring the solution at ambient temperature for 1.5 hours, 1.1 g (0.011 mol) of methyl 4-methoxy-6-methylpyrimidin-2-ylcarbamate was added in one portion. The resulting mixture was heated to reflux under a nitrogen atmosphere for 18 hours. The mixture was then cooled and 50 ml of 5% hydrochloric acid was slowly added. The organic layer was separated and the aqueous layer was extracted with two 50 ml portions of dichloromethane. The organic solutions were combined and washed with 50 ml of saturated sodium chloride solution. After drying over anhydrous magnesium sulfate, the solvents were evaporated to yield 2.2 g of the crude product which was recrystallized to yield 0.4 g of the title compound; m.p. 176°–179° C. The infrared spectrum exhibited a band at 1700 cm$^{-1}$, consistent with the carbonyl group of a sulfonylurea.

NMR (DMSO-d$_6$): δ2.4 (s, 3, pyrimidine CH$_3$); 3.1 (s, 3, OSO$_2$CH$_3$); 3.9 (s, 3, OCH$_3$); 4.4 (s, 4, OCH$_2$CH$_2$O); 6.55 (s, 1, pyrimidine 5-H); 7.1–8.05 (m, 4, aromatic H); 10.45 (broad s, 1, NH); and 13.15 (broad s, 1, NH).

EXAMPLE 4

2-(2-Hydroxyethoxy)benzenesulfonyl isocyanate methanesulfonate ester

A mixture of 15.0 g (0.051 mol) of 2-(2-hydroxyethoxy)benzenesulfonamide methanesulfonate ester and 90 ml of xylenes was heated to reflux to dissolve the sulfonamide. Heating was interrupted while 6.9 ml (6.05 g, 0.061 mol) of n-butyl isocyanate and about 0.1 g of 1,4-diazabicyclo[2.2.2]octane were added. The mixture was heated again to reflux. Approximately 15 ml of condensed phosgene gas was added in portions and heating was continued for about three hours. An additional 10 ml of phosgene was added and heating was stopped. The xylene solution was decanted away from an insoluble brown residue and the xylenes were evaporated under reduced pressure. The presence of the sulfonyl isocyanate group was confirmed by an intense band in the infrared spectrum at 2210 cm$^{-1}$. The crude product was used without further purification.

EXAMPLE 5

N-[4,6-Dimethylpyrimidin-2-yl)aminocarbonyl]-2-(2-hydroxyethoxy)benzenesulfonamide To a suspension of 1.2 g (0.0097 mol) of 2-amino-4,6-dimethylpyrimidine and a few crystals of 1,4-diazabicyclo[2.2.2]octane in 10 ml of dichloromethane was added a solution of approximately 0.01 mol of 2-(2-hydroxyethoxy)benzenesulfonyl isocyanate methanesulfonate ester dissolved in 10 ml of dichloromethane. A mild exotherm was noted upon mixing and a homogeneous solution resulted. The mixture was refluxed for eight hours then stirred at ambient temperature for five days. The solution was filtered and the filtrate was evaporated under reduced pressure. Trituration of the residue with diethyl ether afforded a crude solid which was recrystallized from a mixture of 1-chlorobutane and acetonitrile to yield 2.0 g of the title compound; m.p. 183°–190° C. The infrared spectrum exhibited a broad band at 3390 cm$^{-1}$ consistent with a primary alcohol and a band at 1695 cm$^{-1}$ consistent with the carbonyl group of a sulfonylurea. The mass spectrum exhibited a molecular ion at m/e=366 and fragmentation consistent with the assigned structure.

NMR (DMSO-d$_6$): δ2.45 (s, 6, pyrimidine CH$_3$); 3.7–3.9 (m, 2, -CH$_2$OH); 4.25–4.5 (m, 2, ArOCH$_2$-); 7.05 (s, 1, primidine 5H); 7.05–7.4 and 7.65–8.1 (m, 4, aromatic H); 10.55 (broad s, 1, NH); and 13.2 (broad s, 1, NH).

By the methods discussed above and the examples provided, the following compounds can be made.

TABLE I

| R$_1$ | R$_2$ | R$_3$ | m.p. (°C.) |
|---|---|---|---|
| —CH$_2$CH$_2$—OH | H | H | 183–190° |
| CH$_3$<br>\|<br>—CH—CH$_2$OH | H | H | |
| CH$_3$ CH$_3$<br>\| \|<br>—CH—CH—OH | H | H | |
| CH$_3$ CH$_3$<br>\| \|<br>—CH—C—OH<br>\|<br>CH$_3$ | H | H | |
| CH$_3$<br>\|<br>—CH$_2$—CH—OH | H | H | |
| CH$_3$<br>\|<br>—CH$_2$—C—OH<br>\|<br>CH$_3$ | H | H | |
| —CH$_2$—CH$_2$—CH$_2$—OH | H | H | |
| CH$_3$<br>\|<br>—CH—CH$_2$—CH$_2$—OH | H | H | |
| CH$_3$<br>\|<br>—CH$_2$—CH—CH$_2$—OH | H | H | |
| CH$_3$<br>\|<br>—CH$_2$—CH$_2$—CH—OH | H | H | |
| —CH$_2$—CH$_2$—OH | H | CH$_3$ |  |
| CH$_3$<br>\|<br>—CH—CH$_2$—OH | H | CH$_3$ | |
| CH$_3$ CH$_3$<br>\| \|<br>—CH—CH—OH | H | CH$_3$ | |

TABLE I-continued

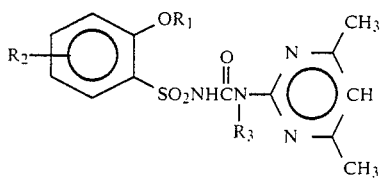

| R₁ | R₂ | R₃ | m.p. (°C.) |
|---|---|---|---|
| -CH(CH₃)-C(CH₃)(OH)-CH₃ | H | CH₃ | |
| -CH₂-CH(CH₃)-OH | H | CH₃ | |
| -CH₂-C(CH₃)(OH)-CH₃ | H | CH₃ | |
| -CH₂-CH₂-CH₂-OH | H | CH₃ | |
| -CH(CH₃)-CH₂-CH₂-OH | H | CH₃ | |
| -CH₂-CH(CH₃)-CH₂-OH | H | CH₃ | |
| -CH₂-CH₂-CH(CH₃)-OH | H | CH₃ | |
| -CH₂-CH₂-OH | 3-F | H | |
| -CH₂-CH₂-OH | 5-F | H | |
| -CH₂-CH₂-OH | 5-Cl | H | |
| -CH₂-CH₂-OH | 5-Br | H | |
| -CH₂-CH₂-OH | 5-CH₃ | H | |
| -CH₂-CH₂-OH | 3-OCH₃ | H | |
| -CH₂-CH₂-OH | 5-OCH₃ | H | |
| -CH₂-CH₂-OH | 6-OCH₃ | H | |
| -CH₂-CH₂-OH | 5-CF₃ | H | |
| -CH₂-CH₂-CH₂-OH | 5-F | H | |
| -CH₂-CH₂-CH₂-OH | 5-Cl | H | |
| -CH₂-CH₂-CH₂-OH | 5-Br | H | |
| -CH₂-CH₂-CH₂-OH | 5-CH₃ | H | |
| -CH₂-CH₂-CH₂-OH | 3-OCH₃ | H | |
| -CH₂-CH₂-CH₂-OH | 5-OCH₃ | H | |
| -CH₂-CH₂-CH₂-OH | 6-OCH₃ | H | |
| -CH₂-CH₂-CH₂-OH | 5-CF₃ | H | |
| -CH(CH₃)-CH₂-OH | 5-CF₃ | H | |
| -CH(CH₃)-CH₂-OH | 5-Br | H | |
| -CH₂CH(CH₃)-OH | 5-CF₃ | H | |
| -CH₂-CH₂-OH | 5-CF₃ | CH₃ | |
| -CH₂-CH₂-OH | 5-Br | CH₃ | |
| -CH₂-CH₂-OH | 3-OCH₃ | CH₃ | |
| -CH₂-CH₂-CH₂-OH | 5-CF₃ | CH₃ | |
| -CH₂-CH₂-OC(O)CH₃ | H | H | |
| -CH₂-CH₂-OC(O)C₂H₅ | H | H | |
| -CH₂-CH₂-OC(O)CH₂-CH₂-CH₃ | H | H | |
| -CH₂-CH₂-OC(O)-CH(CH₃)₂ | H | H | |
| -CH₂-CH₂-OC(O)C₆H₅ | H | H | |
| -CH₂-CH₂-OC(O)NHCH₃ | H | H | |
| -CH₂-CH₂-OC(O)NHC₂H₅ | H | H | |

TABLE I-continued

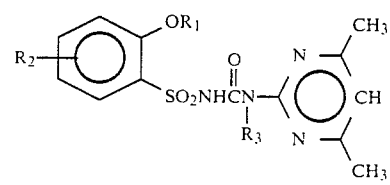

| R₁ | R₂ | R₃ | m.p. (°C.) |
|---|---|---|---|
| -CH₂-CH₂-OC(O)N(CH₃)₂ | H | H | |
| -CH₂-CH₂-OC(O)N(CH₃)(OCH₃) | H | H | |
| -CH₂-CH₂-OC(O)NC₆H₅ | H | H | |
| -CH₂-CH₂-OSO₂CF₃ | H | H | |
| -CH₂-CH₂-OSO₂CH₃ | H | H | |
| -CH₂-CH₂-OSO₂C₂H₅ | H | H | |
| -CH₂-CH₂-OSO₂C₆H₅ | H | H | |
| -CH₂-CH₂-OSO₂-C₆H₄-Br | H | H | |
| -CH₂-CH₂-OSO₂-C₆H₄-CH₃ | H | H | |
| -CH₂-CH₂-OSO₂CH₃ | 5-Br | H | |
| -CH₂-CH₂-OSO₂CH₃ | 5-CF₃ | H | |
| -CH₂-CH₂OSO₂CF₃ | 5-CF₃ | H | |
| -CH₂-CH₂-OC(O)CH₃ | 5-CF₃ | H | |
| -CH₂-CH₂-OSO₂CH₃ | H | CH₃ | |
| -CH₂-CH₂-OC(O)CH₃ | H | CH₃ | |
| -CH₂-CH₂-CH₂-OSO₂CH₃ | 5-CF₃ | H | |
| -CH₂-CH₂-CH₂-OSO₂CH₃ | H | CH₃ | |
| -CH₂-CH₂-CH₂-OC(O)CH₃ | H | CH₃ | |
| -CH₂CH(CH₃)-OSO₂CH₃ | H | H | |
| -CH(CH₃)-CH(CH₃)-OSO₂CH₃ | H | H | |
| -CH₂CH₂-CH(CH₃)-OSO₂CH₃ | H | H | |
| -CH₂CH(CH₃)CH₂-OSO₂CH₃ | H | H | |

TABLE II

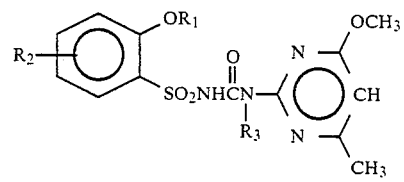

| R₁ | R₂ | R₃ | m.p. (°C.) |
|---|---|---|---|
| -CH₂CH₂-OH | H | H | 200-204° |
| -CH(CH₃)-CH₂OH | H | H | |
| -CH(CH₃)-CH(CH₃)-OH | H | H | |

TABLE II-continued

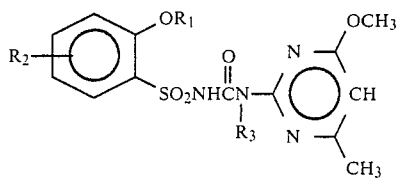

| $R_1$ | $R_2$ | $R_3$ | m.p. (°C.) |
|---|---|---|---|
| -CH(CH₃)-C(CH₃)₂-OH | H | H | |
| -CH₂-CH(CH₃)-OH | H | H | |
| -CH₂-C(CH₃)₂-OH | H | H | |
| -CH₂-CH₂-CH₂-OH | H | H | |
| -CH(CH₃)-CH₂-CH₂-OH | H | H | |
| -CH₂-CH(CH₃)-CH₂-OH | H | H | |
| -CH₂-CH₂-CH(CH₃)-OH | H | H | |
| -CH₂-CH₂-OH | H | CH₃ | |
| -CH₂-CH(CH₃)-OH | H | CH₃ | |
| -CH(CH₃)-CH(CH₃)-OH | H | CH₃ | |
| -CH(CH₃)-C(CH₃)₂-OH | H | CH₃ | |
| -CH₂-CH(CH₃)-OH | H | CH₃ | |
| -CH₂-C(CH₃)₂-OH | H | CH₃ | |
| -CH₂-CH₂-CH₂-OH | H | CH₃ | |
| -CH(CH₃)-CH₂-CH₂-OH | H | CH₃ | |
| -CH₂-CH(CH₃)-CH₂-OH | H | CH₃ | |
| -CH₂-CH₂-CH(CH₃)-OH | H | CH₃ | |
| -CH₂-CH₂-OH | 3-F | H | |

TABLE II-continued

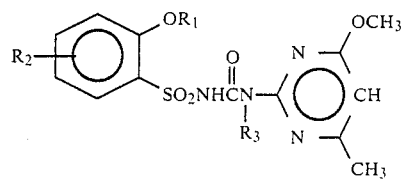

| $R_1$ | $R_2$ | $R_3$ | m.p. (°C.) |
|---|---|---|---|
| -CH₂-CH₂-OH | 5-F | H | |
| -CH₂-CH₂-OH | 5-Cl | H | |
| -CH₂-CH₂-OH | 5-Br | H | |
| -CH₂-CH₂-OH | 5-CH₃ | H | |
| -CH₂-CH₂-OH | 3-OCH₃ | H | |
| -CH₂-CH₂-OH | 5-OCH₃ | H | |
| -CH₂-CH₂-OH | 6-OCH₃ | H | |
| -CH₂-CH₂-OH | 5-CF₃ | H | |
| -CH₂-CH₂-CH₂-OH | 5-F | H | |
| -CH₂-CH₂-CH₂-OH | 5-Cl | H | |
| -CH₂-CH₂-CH₂-OH | 5-Br | H | |
| -CH₂-CH₂-CH₂-OH | 5-CH₃ | H | |
| -CH₂-CH₂-CH₂-OH | 3-OCH₃ | H | |
| -CH₂-CH₂-CH₂-OH | 5-OCH₃ | H | |
| -CH₂-CH₂-CH₂-OH | 6-OCH₃ | H | |
| -CH₂-CH₂-CH₂-OH | 5-CF₃ | H | |
| -CH(CH₃)-CH₂-OH | 5-CF₃ | H | |
| -CH(CH₃)-CH₂-OH | 5-Br | H | |
| -CH₂CH(CH₃)-OH | 5-CF₃ | H | |
| -CH₂-CH₂-OH | 5-CF₃ | CH₃ | |
| -CH₂-CH₂-OH | 5-Br | CH₃ | |
| -CH₂-CH₂-OH | 3-OCH₃ | CH₃ | |
| -CH₂-CH₂-CH₂-OH | 5-CF₃ | CH₃ | |
| -CH₂-CH₂-OC(O)CH₃ | H | H | |
| -CH₂-CH₂-OC(O)C₂H₅ | H | H | |
| -CH₂-CH₂-OC(O)CH₂-CH₂-CH₃ | H | H | |
| -CH₂-CH₂-OC(O)-CH(CH₃)₂ | H | H | |
| -CH₂-CH₂-OC(O)C₆H₅ | H | H | |
| -CH₂-CH₂-OC(O)NHCH₃ | H | H | |
| -CH₂-CH₂-OC(O)NHC₂H₅ | H | H | |
| -CH₂-CH₂-OC(O)N(CH₃)₂ | H | H | |
| -CH₂-CH₂-OC(O)N(CH₃)(OCH₃) | H | H | |
| -CH₂-CH₂-OC(O)NC₆H₅ | H | H | |
| -CH₂-CH₂-OSO₂CF₃ | H | H | |
| -CH₂-CH₂-OSO₂CH₃ | H | H | 176-179° |
| -CH₂-CH₂-OSO₂C₂H₅ | H | H | |
| -CH₂-CH₂-OSO₂C₆H₅ | H | H | |
| -CH₂-CH₂-OSO₂-C₆H₄-Br | H | H | |
| -CH₂-CH₂-OSO₂-C₆H₄-CH₃ | H | H | |
| -CH₂-CH₂-OSO₂CH₃ | 5-Br | H | |
| -CH₂-CH₂-OSO₂CH₃ | 5-CF₃ | H | |
| -CH₂-CH₂OSO₂CF₃ | 5-CF₃ | H | |
| -CH₂-CH₂-OC(O)CH₃ | 5-CF₃ | H | |
| -CH₂-CH₂-OSO₂CH₃ | H | CH₃ | |
| -CH₂-CH₂-OC(O)CH₃ | H | CH₃ | |
| -CH₂-CH₂-CH₂-OSO₂CH₃ | 5-CF₃ | H | |
| -CH₂-CH₂-CH₂-OSO₂CH₃ | H | CH₃ | |
| -CH₂-CH₂-CH₂-OC(O)CH₃ | H | CH₃ | |

TABLE II-continued

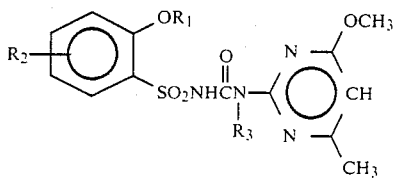

| R1 | R2 | R3 | m.p. (°C.) |
|---|---|---|---|
| −CH₂CH(CH₃)−OSO₂CH₃ | H | H | |
| −CH(CH₃)−CH(CH₃)−OSO₂CH₃ | H | H | |
| −CH₂CH₂−CH(CH₃)−OSO₂CH₃ | H | H | |
| −CH₂CH(CH₃)CH₂−OSO₂CH₃ | H | H | |

TABLE III

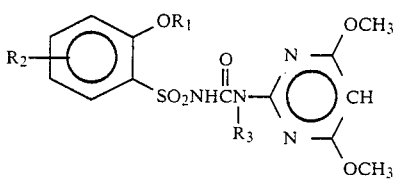

| R1 | R2 | R3 | m.p. (°C.) |
|---|---|---|---|
| −CH₂CH₂−OH | H | H | 195−199° |
| −CH(CH₃)−CH₂OH | H | H | |
| −CH(CH₃)−CH(CH₃)−OH | H | H | |
| −CH(CH₃)−C(CH₃)₂−OH | H | H | |
| −CH₂−CH(CH₃)−OH | H | H | |
| −CH₂−C(CH₃)₂−OH | H | H | |
| −CH₂−CH₂−CH₂−OH | H | H | |
| −CH(CH₃)−CH₂−CH₂−OH | H | H | |
| −CH₂−CH(CH₃)−CH₂−OH | H | H | |

TABLE III-continued

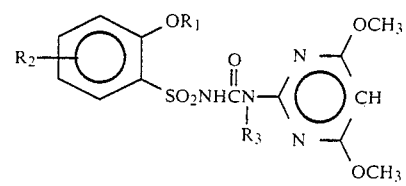

| R1 | R2 | R3 | m.p. (°C.) |
|---|---|---|---|
| −CH₂−CH₂−CH(CH₃)−OH | H | H | |
| −CH₂−CH₂−OH | H | CH₃ | |
| −CH(CH₃)−CH₂−OH | H | CH₃ | |
| −CH(CH₃)−CH(CH₃)−OH | H | CH₃ | |
| −CH(CH₃)−C(CH₃)₂−OH | H | CH₃ | |
| −CH₂−CH(CH₃)−OH | H | CH₃ | |
| −CH₂−C(CH₃)₂−OH | H | CH₃ | |
| −CH₂−CH₂−CH₂−OH | H | CH₃ | |
| −CH(CH₃)−CH₂−CH₂−OH | H | CH₃ | |
| −CH₂−CH(CH₃)−CH₂−OH | H | CH₃ | |
| −CH₂−CH₂−CH(CH₃)−OH | H | CH₃ | |
| −CH₂−CH₂OH | 3-F | H | |
| −CH₂−CH₂−OH | 5-F | H | |
| −CH₂−CH₂−OH | 5-Cl | H | |
| −CH₂−CH₂−OH | 5-Br | H | |
| −CH₂−CH₂−OH | 5-CH₃ | H | |
| −CH₂−CH₂−OH | 3-OCH₃ | H | |
| −CH₂−CH₂−OH | 5-OCH₃ | H | |
| −CH₂−CH₂−OH | 6-OCH₃ | H | |
| −CH₂−CH₂−OH | 5-CF₃ | H | |
| −CH₂−CH₂−CH₂−OH | 5-F | H | |
| −CH₂−CH₂−CH₂−OH | 5-Cl | H | |
| −CH₂−CH₂−CH₂−OH | 5-Br | H | |
| −CH₂−CH₂−CH₂−OH | 5-CH₃ | H | |
| −CH₂−CH₂−CH₂−OH | 3-OCH₃ | H | |
| −CH₂−CH₂−CH₂−OH | 5-OCH₃ | H | |
| −CH₂−CH₂−CH₂−OH | 6-OCH₃ | H | |
| −CH₂−CH₂−CH₂−OH | 5-CF₃ | H | |
| −CH(CH₃)−CH₂−OH | 5-CF₃ | H | |
| −CH(CH₃)−CH₂−OH | 5-Br | H | |

TABLE III-continued

Structure: Phenyl ring with $OR_1$ (ortho) and $R_2$ substituents, bearing $-SO_2NHC(O)N(R_3)-$ linked to a pyrimidine ring with $OCH_3$ (4), $CH$ (5), $OCH_3$ (6) substituents.

| $R_1$ | $R_2$ | $R_3$ | m.p. (°C) |
|---|---|---|---|
| $-CH_2CH(CH_3)-OH$ | 5-$CF_3$ | H | |
| $-CH_2-CH_2-OH$ | 5-$CF_3$ | $CH_3$ | |
| $-CH_2-CH_2-OH$ | 5-Br | $CH_3$ | |
| $-CH_2-CH_2-OH$ | 3-$OCH_3$ | $CH_3$ | |
| $-CH_2-CH_2-CH_2-OH$ | 5-$CF_3$ | $CH_3$ | |
| $-CH_2-CH_2-OC(O)CH_3$ | H | H | |
| $-CH_2-CH_2-OC(O)C_2H_5$ | H | H | |
| $-CH_2-CH_2-OC(O)OCH_2-CH_2-CH_3$ | H | H | |
| $-CH_2-CH_2-OC(O)-CH(CH_3)_2$ | H | H | |
| $-CH_2-CH_2-OC(O)C_6H_5$ | H | H | |
| $-CH_2-CH_2-OC(O)NHCH_3$ | H | H | |
| $-CH_2-CH_2-OC(O)NHC_2H_5$ | H | H | |
| $-CH_2-CH_2-OC(O)N(CH_3)_2$ | H | H | |
| $-CH_2-CH_2-OC(O)N(CH_3)_2$ | H | H | |
| $-CH_2-CH_2-OC(O)NC_6H_5$ | H | H | |
| $-CH_2-CH_2-OSO_2CF_3$ | H | H | |
| $-CH_2-CH_2-OSO_2CH_3$ | H | H | |
| $-CH_2-CH_2-OSO_2C_2H_5$ | H | H | |
| $-CH_2-CH_2-OSO_2C_6H_5$ | H | H | |
| $-CH_2-CH_2-OSO_2-C_6H_4-Br$ | H | H | |
| $-CH_2-CH_2-OSO_2-C_6H_4-CH_3$ | H | H | |
| $-CH_2-CH_2-OSO_2CH_3$ | 5-Br | H | |
| $-CH_2-CH_2-OSO_2CH_3$ | 5-$CF_3$ | H | |
| $-CH_2-CH_2OSO_2CF_3$ | 5-$CF_3$ | H | |
| $-CH_2-CH_2-OC(O)CH_3$ | 5-$CF_3$ | H | |
| $-CH_2-CH_2-OSO_2CH_3$ | H | $CH_3$ | |
| $-CH_2-CH_2-OC(O)CH_3$ | H | $CH_3$ | |
| $-CH_2-CH_2-CH_2-OSO_2CH_3$ | 5-$CF_3$ | H | |
| $-CH_2-CH_2-CH_2-OSO_2CH_3$ | H | $CH_3$ | |
| $-CH_2-CH_2-CH_2-OC(O)CH_3$ | H | $CH_3$ | |
| $-CH_2CH(CH_3)-OSO_2CH_3$ | H | H | |
| $-CH(CH_3)CH(CH_3)-OSO_2CH_3$ | H | H | |
| $-CH_2CH_2-CH(CH_3)-OSO_2CH_3$ | H | H | |
| $-CH_2CH(CH_3)CH_2-OSO_2CH_3$ | H | H | |

TABLE IV

Structure: Phenyl ring with $OR_1$ (ortho) and $R_2$ substituents, bearing $-SO_2NHC(O)N(R_3)-$ linked to a pyrimidine ring with $CH_3$ (4) and $CH_3$ (6) substituents.

| $R_1$ | $R_2$ | $R_3$ | m.p. (°C) |
|---|---|---|---|
| $-CH_2CH_2-OH$ | H | H | |
| $-CH(CH_3)-CH_2OH$ | H | H | |
| $-CH(CH_3)-CH(CH_3)-OH$ | H | H | |
| $-CH(CH_3)-C(CH_3)_2-OH$ | H | H | |
| $-CH_2-CH(CH_3)-OH$ | H | H | |
| $-CH_2-C(CH_3)_2-OH$ | H | H | |
| $-CH_2-CH_2-CH_2-OH$ | H | H | |
| $-CH(CH_3)-CH_2-CH_2-OH$ | H | H | |
| $-CH_2-CH(CH_3)-CH_2-OH$ | H | H | |
| $-CH_2-CH_2-CH(CH_3)-OH$ | H | H | |
| $-CH_2-CH_2-OH$ | H | $CH_3$ | |
| $-CH(CH_3)-CH_2-OH$ | H | $CH_3$ | |
| $-CH(CH_3)-CH(CH_3)-OH$ | H | $CH_3$ | |
| $-CH(CH_3)-C(CH_3)_2-OH$ | H | $CH_3$ | |
| $-CH_2-CH(CH_3)-OH$ | H | $CH_3$ | |
| $-CH_2-C(CH_3)_2-OH$ | H | $CH_3$ | |
| $-CH_2-CH_2-CH_2-OH$ | H | $CH_3$ | |
| $-CH(CH_3)-CH_2-CH_2-OH$ | H | $CH_3$ | |

TABLE IV-continued

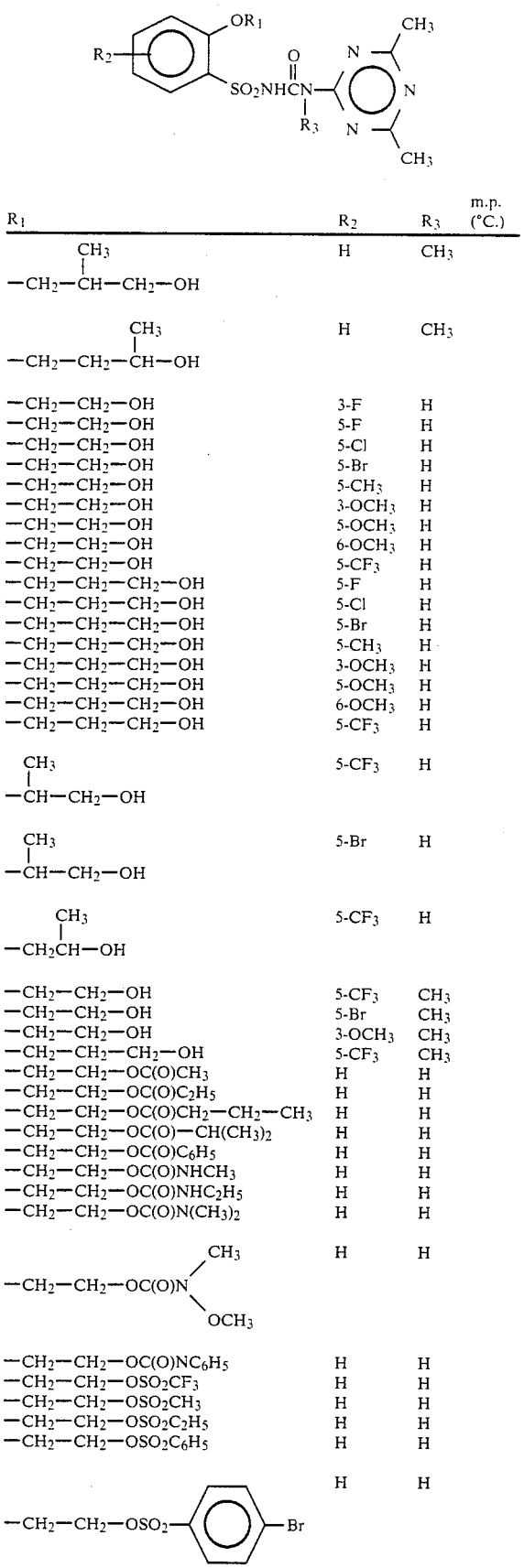

| R₁ | R₂ | R₃ | m.p. (°C.) |
|---|---|---|---|
| −CH₂−CH(CH₃)−CH₂−OH | H | CH₃ | |
| −CH₂−CH₂−CH(CH₃)−OH | H | CH₃ | |
| −CH₂−CH₂−OH | 3-F | H | |
| −CH₂−CH₂−OH | 5-F | H | |
| −CH₂−CH₂−OH | 5-Cl | H | |
| −CH₂−CH₂−OH | 5-Br | H | |
| −CH₂−CH₂−OH | 5-CH₃ | H | |
| −CH₂−CH₂−OH | 3-OCH₃ | H | |
| −CH₂−CH₂−OH | 5-OCH₃ | H | |
| −CH₂−CH₂−OH | 6-OCH₃ | H | |
| −CH₂−CH₂−OH | 5-CF₃ | H | |
| −CH₂−CH₂−CH₂−OH | 5-F | H | |
| −CH₂−CH₂−CH₂−OH | 5-Cl | H | |
| −CH₂−CH₂−CH₂−OH | 5-Br | H | |
| −CH₂−CH₂−CH₂−OH | 5-CH₃ | H | |
| −CH₂−CH₂−CH₂−OH | 3-OCH₃ | H | |
| −CH₂−CH₂−CH₂−OH | 5-OCH₃ | H | |
| −CH₂−CH₂−CH₂−OH | 6-OCH₃ | H | |
| −CH₂−CH₂−CH₂−OH | 5-CF₃ | H | |
| −CH(CH₃)−CH₂−OH | 5-CF₃ | H | |
| −CH(CH₃)−CH₂−OH | 5-Br | H | |
| −CH₂CH(CH₃)−OH | 5-CF₃ | H | |
| −CH₂−CH₂−OH | 5-CF₃ | CH₃ | |
| −CH₂−CH₂−OH | 5-Br | CH₃ | |
| −CH₂−CH₂−OH | 3-OCH₃ | CH₃ | |
| −CH₂−CH₂−CH₂−OH | 5-CF₃ | CH₃ | |
| −CH₂−CH₂−OC(O)CH₃ | H | H | |
| −CH₂−CH₂−OC(O)C₂H₅ | H | H | |
| −CH₂−CH₂−OC(O)CH₂−CH₂−CH₃ | H | H | |
| −CH₂−CH₂−OC(O)−CH(CH₃)₂ | H | H | |
| −CH₂−CH₂−OC(O)C₆H₅ | H | H | |
| −CH₂−CH₂−OC(O)NHCH₃ | H | H | |
| −CH₂−CH₂−OC(O)NHC₂H₅ | H | H | |
| −CH₂−CH₂−OC(O)N(CH₃)₂ | H | H | |
| −CH₂−CH₂−OC(O)N(CH₃)(OCH₃) | H | H | |
| −CH₂−CH₂−OC(O)NC₆H₅ | H | H | |
| −CH₂−CH₂−OSO₂CF₃ | H | H | |
| −CH₂−CH₂−OSO₂CH₃ | H | H | |
| −CH₂−CH₂−OSO₂C₂H₅ | H | H | |
| −CH₂−CH₂−OSO₂C₆H₅ | H | H | |
| −CH₂−CH₂−OSO₂−C₆H₄−Br | H | H | |

TABLE IV-continued

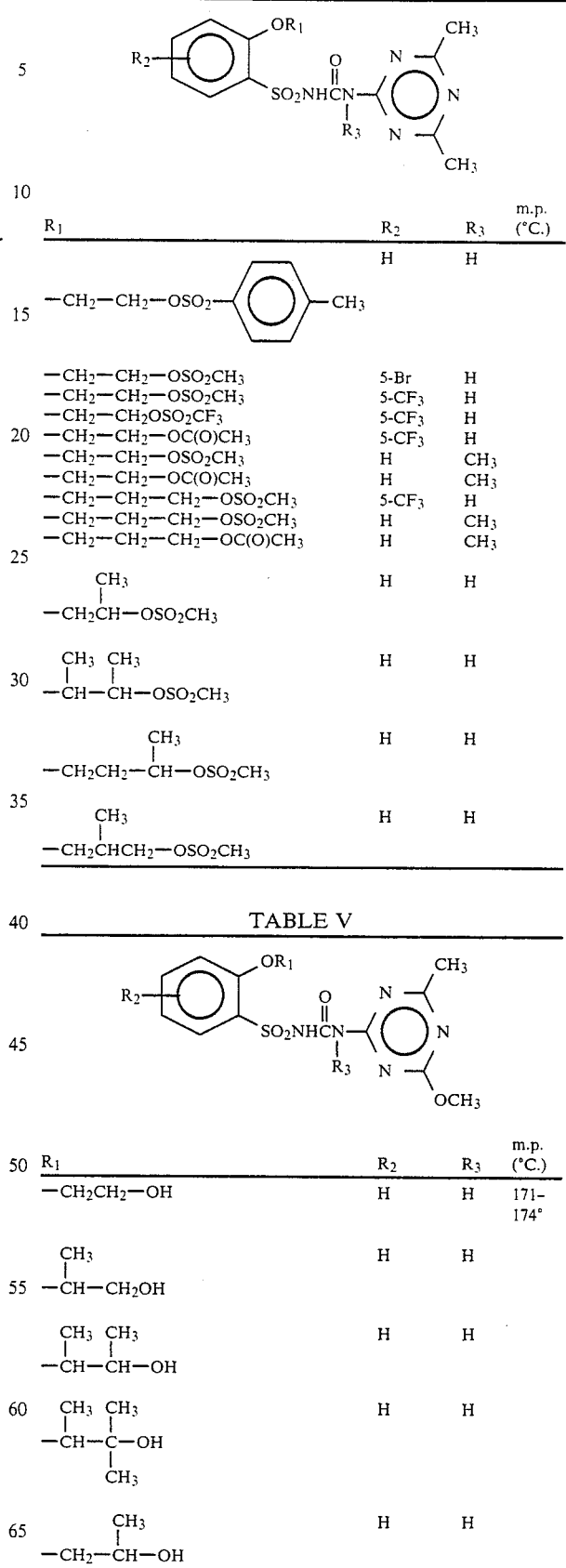

| R₁ | R₂ | R₃ | m.p. (°C.) |
|---|---|---|---|
| −CH₂−CH₂−OSO₂−C₆H₄−CH₃ | H | H | |
| −CH₂−CH₂−OSO₂CH₃ | 5-Br | H | |
| −CH₂−CH₂−OSO₂CH₃ | 5-CF₃ | H | |
| −CH₂−CH₂OSO₂CF₃ | 5-CF₃ | H | |
| −CH₂−CH₂−OC(O)CH₃ | 5-CF₃ | H | |
| −CH₂−CH₂−OSO₂CH₃ | H | CH₃ | |
| −CH₂−CH₂−OC(O)CH₃ | H | CH₃ | |
| −CH₂−CH₂−CH₂−OSO₂CH₃ | 5-CF₃ | H | |
| −CH₂−CH₂−CH₂−OSO₂CH₃ | H | CH₃ | |
| −CH₂−CH₂−CH₂−OC(O)CH₃ | H | CH₃ | |
| −CH₂CH(CH₃)−OSO₂CH₃ | H | H | |
| −CH(CH₃)−CH(CH₃)−OSO₂CH₃ | H | H | |
| −CH₂CH₂−CH(CH₃)−OSO₂CH₃ | H | H | |
| −CH₂CH(CH₃)CH₂−OSO₂CH₃ | H | H | |

TABLE V

| R₁ | R₂ | R₃ | m.p. (°C.) |
|---|---|---|---|
| −CH₂CH₂−OH | H | H | 171–174° |
| −CH(CH₃)−CH₂OH | H | H | |
| −CH(CH₃)−CH(CH₃)−OH | H | H | |
| −CH(CH₃)−C(CH₃)₂−OH | H | H | |
| −CH₂−CH(CH₃)−OH | H | H | |

TABLE V-continued $$R_2 \underset{}{\overset{OR_1}{\diagdown}} \text{C}_6\text{H}_3\text{-SO}_2\text{NHC(O)N(R}_3\text{)-pyrimidine(CH}_3\text{, OCH}_3\text{)}$$

| R₁ | R₂ | R₃ | m.p. (°C.) |
|---|---|---|---|
| —CH₂—C(CH₃)₂—OH | H | H | |
| —CH₂—CH₂—CH₂—OH | H | H | |
| —CH(CH₃)—CH₂—CH₂—OH | H | H | |
| —CH₂—CH(CH₃)—CH₂—OH | H | H | |
| —CH₂—CH₂—CH(CH₃)—OH | H | H | |
| —CH₂—CH₂—OH | H | CH₃ | |
| —CH(CH₃)—CH₂—OH | H | CH₃ | |
| —CH(CH₃)—CH(CH₃)—OH | H | CH₃ | |
| —CH(CH₃)—C(CH₃)₂—OH | H | CH₃ | |
| —CH₂—CH(CH₃)—OH | H | CH₃ | |
| —CH₂—C(CH₃)₂—OH | H | CH₃ | |
| —CH₂—CH₂—CH₂—OH | H | CH₃ | |
| —CH(CH₃)—CH₂—CH₂—OH | H | CH₃ | |
| —CH₂—CH(CH₃)—CH₂—OH | H | CH₃ | |
| —CH₂—CH₂—CH(CH₃)—OH | H | CH₃ | |
| —CH₂—CH₂—OH | 3-F | H | |
| —CH₂—CH₂—OH | 5-F | H | |
| —CH₂—CH₂—OH | 5-Cl | H | |
| —CH₂—CH₂—OH | 5-Br | H | |
| —CH₂—CH₂—OH | 5-CH₃ | H | |
| —CH₂—CH₂—OH | 3-OCH₃ | H | |
| —CH₂—CH₂—OH | 5-OCH₃ | H | |
| —CH₂—CH₂—OH | 6-OCH₃ | H | |
| —CH₂—CH₂—OH | 5-CF₃ | H | |
| —CH₂—CH₂—CH₂—OH | 5-F | H | |
| —CH₂—CH₂—CH₂—OH | 5-Cl | H | |
| —CH₂—CH₂—CH₂—OH | 5-Br | H | |
| —CH₂—CH₂—CH₂—OH | 5-CH₃ | H | |
| —CH₂—CH₂—CH₂—OH | 3-OCH₃ | H | |
| —CH₂—CH₂—CH₂—OH | 5-OCH₃ | H | |
| —CH₂—CH₂—CH₂—OH | 6-OCH₃ | H | |
| —CH₂—CH₂—CH₂—OH | 5-CF₃ | H | |
| —CH(CH₃)—CH₂—OH | 5-CF₃ | H | |
| —CH(CH₃)—CH₂—OH | 5-Br | H | |
| —CH₂—CH(CH₃)—OH | 5-CF₃ | H | |
| —CH₂—CH₂—OH | 5-CF₃ | CH₃ | |
| —CH₂—CH₂—OH | 5-Br | CH₃ | |
| —CH₂—CH₂—OH | 3-OCH₃ | CH₃ | |
| —CH₂—CH₂—CH₂—OH | 5-CF₃ | CH₃ | |
| —CH₂—CH₂—OC(O)CH₃ | H | H | |
| —CH₂—CH₂—OC(O)C₂H₅ | H | H | |
| —CH₂—CH₂—OC(O)CH₂—CH₂—CH₃ | H | H | |
| —CH₂—CH₂—OC(O)—CH(CH₃)₂ | H | H | |
| —CH₂—CH₂—OC(O)C₆H₅ | H | H | |
| —CH₂—CH₂—OC(O)NHCH₃ | H | H | |
| —CH₂—CH₂—OC(O)NHC₂H₅ | H | H | |
| —CH₂—CH₂—OC(O)N(CH₃)₂ | H | H | |
| —CH₂—CH₂—OC(O)N(CH₃)₂ | H | H | |
| —CH₂—CH₂—OC(O)NC₆H₅ | H | H | |
| —CH₂—CH₂—OSO₂CF₃ | H | H | |
| —CH₂—CH₂—OSO₂CH₃ | H | H | |
| —CH₂—CH₂—OSO₂C₂H₅ | H | H | |
| —CH₂—CH₂—OSO₂C₆H₅ | H | H | |
| —CH₂—CH₂—OSO₂—C₆H₄—Br | H | H | |
| —CH₂—CH₂—OSO₂—C₆H₄—CH₃ | H | H | |
| —CH₂—CH₂—OSO₂CH₃ | 5-Br | H | |
| —CH₂—CH₂—OSO₂CH₃ | 5-CF₃ | H | |
| —CH₂—CH₂OSO₂CF₃ | 5-CF₃ | H | |
| —CH₂—CH₂—OC(O)CH₃ | 5-CF₃ | H | |
| —CH₂—CH₂—OSO₂CH₃ | H | CH₃ | |
| —CH₂—CH₂—OC(O)CH₃ | H | CH₃ | |
| —CH₂—CH₂—OSO₂CH₃ | 5-CF₃ | CH₃ | |
| —CH₂—CH₂—CH₂—OSO₂CH₃ | H | CH₃ | |
| —CH₂—CH₂—CH₂—OC(O)CH₃ | H | CH₃ | |
| —CH₂CH(CH₃)—OSO₂CH₃ | H | H | |

TABLE V-continued

Structure: phenyl with OR₁ (ortho), R₂ substituent, SO₂NHC(O)N(R₃)- linked to pyrimidine with CH₃ and OCH₃ groups

| R₁ | R₂ | R₃ | m.p. (°C.) |
|---|---|---|---|
| $-\underset{CH_3}{CH}-\underset{CH_3}{CH}-OSO_2CH_3$ | H | H | |
| $-CH_2CH_2-\underset{CH_3}{CH}-OSO_2CH_3$ | H | H | |
| $-CH_2\underset{CH_3}{CH}CH_2-OSO_2CH_3$ | H | H | |

TABLE VI

Structure: phenyl with OR₁ (ortho), R₂ substituent, SO₂NHC(O)N(R₃)- linked to pyrimidine with two OCH₃ groups

| R₁ | R₂ | R₃ | m.p. (°C.) |
|---|---|---|---|
| —CH₂CH₂—OH | H | H | 159–165° |
| $-\underset{CH_3}{CH}-CH_2OH$ | H | H | |
| $-\underset{CH_3}{CH}-\underset{CH_3}{CH}-OH$ | H | H | |
| $-\underset{CH_3}{CH}-\underset{\underset{CH_3}{|}}{C}(CH_3)-OH$ | H | H | |
| $-CH_2-\underset{CH_3}{CH}-OH$ | H | H | |
| $-CH_2-\underset{\underset{CH_3}{|}}{C}(CH_3)-OH$ | H | H | |
| —CH₂—CH₂—CH₂—OH | H | H | |
| $-\underset{CH_3}{CH}-CH_2-CH_2-OH$ | H | H | |
| $-CH_2-\underset{CH_3}{CH}-CH_2-OH$ | H | H | |
| $-CH_2-CH_2-\underset{CH_3}{CH}-OH$ | H | H | |
| —CH₂—CH₂—OH | H | CH₃ |
| $-\underset{CH_3}{CH}-CH_2-OH$ | H | CH₃ |
| $-\underset{CH_3}{CH}-\underset{CH_3}{CH}-OH$ | H | CH₃ |
| $-\underset{CH_3}{CH}-\underset{\underset{CH_3}{|}}{C}(CH_3)-OH$ | H | CH₃ |
| $-CH_2-\underset{CH_3}{CH}-OH$ | H | CH₃ |
| $-CH_2-\underset{\underset{CH_3}{|}}{C}(CH_3)-OH$ | H | CH₃ |
| —CH₂—CH₂—CH₂—OH | H | CH₃ |
| $-\underset{CH_3}{CH}-CH_2-CH_2-OH$ | H | CH₃ |
| $-CH_2-\underset{CH_3}{CH}-CH_2-OH$ | H | CH₃ |
| $-CH_2-CH_2-\underset{CH_3}{CH}-OH$ | H | CH₃ |
| —CH₂—CH₂—OH | 3-F | H |
| —CH₂—CH₂—OH | 5-F | H |
| —CH₂—CH₂—OH | 5-Cl | H |
| —CH₂—CH₂—OH | 5-Br | H |
| —CH₂—CH₂—OH | 5-CH₃ | H |
| —CH₂—CH₂—OH | 3-OCH₃ | H |
| —CH₂—CH₂—OH | 5-OCH₃ | H |
| —CH₂—CH₂—OH | 6-OCH₃ | H |
| —CH₂—CH₂—OH | 5-CF₃ | H |
| —CH₂—CH₂—CH₂—OH | 5-F | H |
| —CH₂—CH₂—CH₂—OH | 5-Cl | H |
| —CH₂—CH₂—CH₂—OH | 5-Br | H |
| —CH₂—CH₂—CH₂—OH | 5-CH₃ | H |
| —CH₂—CH₂—CH₂—OH | 3-OCH₃ | H |
| —CH₂—CH₂—CH₂—OH | 5-OCH₃ | H |
| —CH₂—CH₂—CH₂—OH | 6-OCH₃ | H |
| —CH₂—CH₂—CH₂—OH | 5-CF₃ | H |
| $-\underset{CH_3}{CH}-CH_2-OH$ | 5-CF₃ | H |
| $-\underset{CH_3}{CH}-CH_2-OH$ | 5-Br | H |
| $-CH_2\underset{CH_3}{CH}-OH$ | 5-CF₃ | H |
| —CH₂—CH₂—OH | 5-CF₃ | CH₃ |
| —CH₂—CH₂—OH | 5-Br | CH₃ |
| —CH₂—CH₂—OH | 3-OCH₃ | CH₃ |

TABLE VI-continued

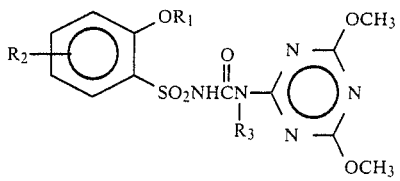

| R₁ | R₂ | R₃ | m.p. (°C.) |
|---|---|---|---|
| —CH₂—CH₂—CH₂—OH | 5-CF₃ | CH₃ | |
| —CH₂—CH₂—OC(O)CH₃ | H | H | |
| —CH₂—CH₂—OC(O)C₂H₅ | H | H | |
| —CH₂—CH₂—OC(O)CH₂—CH₂—CH₃ | H | H | |
| —CH₂—CH₂—OC(O)—CH(CH₃)₂ | H | H | |
| —CH₂—CH₂—OC(O)C₆H₅ | H | H | |
| —CH₂—CH₂—OC(O)NHCH₃ | H | H | |
| —CH₂—CH₂—OC(O)NHC₂H₅ | H | H | |
| —CH₂—CH₂—OC(O)N(CH₃)₂ | H | H | |
| —CH₂—CH₂—OC(O)N(CH₃)(OCH₃) | H | H | |
| —CH₂—CH₂—OC(O)NC₆H₅ | H | H | |
| —CH₂—CH₂—OSO₂CF₃ | H | H | |
| —CH₂—CH₂—OSO₂CH₃ | H | H | |
| —CH₂—CH₂—OSO₂C₂H₅ | H | H | |
| —CH₂—CH₂—OSO₂C₆H₅ | H | H | |
| —CH₂—CH₂—OSO₂-(4-Br-C₆H₄) | H | H | |
| —CH₂—CH₂—OSO₂-(4-CH₃-C₆H₄) | H | H | |
| —CH₂—CH₂—OSO₂CH₃ | 5-Br | H | |
| —CH₂—CH₂—OSO₂CH₃ | 5-CF₃ | H | |
| —CH₂—CH₂OSO₂CF₃ | 5-CF₃ | H | |
| —CH₂—CH₂—OC(O)CH₃ | 5-CF₃ | H | |
| —CH₂—CH₂—OSO₂CH₃ | H | CH₃ | |
| —CH₂—CH₂—OC(O)CH₃ | H | CH₃ | |
| —CH₂—CH₂—CH₂—OSO₂CH₃ | 5-CF₃ | H | |
| —CH₂—CH₂—OSO₂CH₃ | H | CH₃ | |
| —CH₂—CH₂—CH₂—OC(O)CH₃ | H | CH₃ | |
| —CH₂CH(CH₃)—OSO₂CH₃ | H | H | |
| —CH(CH₃)—CH(CH₃)—OSO₂CH₃ | H | H | |
| —CH₂CH₂CH(CH₃)—OSO₂CH₃ | H | H | |
| —CH₂CH(CH₃)CH₂—OSO₂CH₃ | H | H | |

TABLE VII

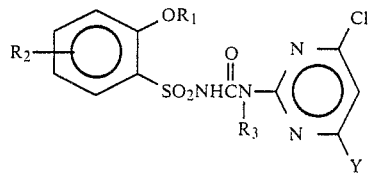

| R₁ | R₂ | R₃ | Y | m.p. (°C.) |
|---|---|---|---|---|
| —CH₂CH₂—OH | H | H | OCH₃ | |
| —CH(CH₃)CH₂OH | H | H | OCH₃ | |
| —CH(CH₃)CH(CH₃)—OH | H | H | OCH₃ | |
| —CH(CH₃)C(CH₃)₂—OH | H | H | OCH₃ | |
| —CH₂CH(CH₃)—OH | H | H | OCH₃ | |
| —CH₂C(CH₃)₂—OH | H | H | OCH₃ | |
| —CH₂—CH₂—CH₂—OH | H | H | OCH₃ | |
| —CH(CH₃)—CH₂—CH₂—OH | H | H | OCH₃ | |
| —CH₂—CH(CH₃)—CH₂—OH | H | H | OCH₃ | |
| —CH₂—CH₂—CH(CH₃)—OH | H | H | OCH₃ | |
| —CH₂CH₂—OSO₂CH₃ | H | H | OCH₃ | |
| —CH₂—CH₂—CH₂—OSO₂CH₃ | H | H | OCH₃ | |
| —CH₂—CH₂—OC(O)CH₃ | H | H | OCH₃ | |
| —CH₂—CH₂—CH₂OC(O)C₂H₅ | H | H | OCH₃ | |
| —CH₂—CH₂—OC(O)NHCH₃ | H | H | OCH₃ | |
| —CH₂—CH₂—OSO₂CF₃ | H | H | OCH₃ | |
| —CH₂—CH₂—OH | H | CH₃ | OCH₃ | |
| —CH₂—CH₂—CH₂—OH | H | CH₃ | OCH₃ | |
| —CH₂—CH₂—OSO₂CH₃ | H | CH₃ | OCH₃ | |
| —CH₂—CH₂—OH | 3-OCH₃ | H | OCH₃ | |
| —CH₂—CH₂—OH | 5-CF₃ | H | OCH₃ | |
| —CH₂—CH₂—CH₂—OH | 5-CF₃ | H | OCH₃ | |
| —CH₂—CH₂—OSO₂CH₃ | 5-CF₃ | H | OCH₃ | |
| —CH₂—CH₂—OSO₂CH₃ | 5-CF₃ | CH₃ | OCH₃ | |
| —CH₂—CH₂OC(O)CH₃ | 5-CF₃ | H | OCH₃ | |
| —CH₂—CH₂—OH | H | H | CH₃ | |
| —CH₂—CH₂—OH | H | H | OC₂H₅ | |
| —CH₂—CH₂—OH | H | H | NH₂ | |
| —CH₂—CH₂—OH | H | H | NHCH₃ | |
| —CH₂—CH₂—OH | H | H | N(CH₃)₂ | |
| —CH₂—CH₂—OH | 5-CF₃ | H | NH₂ | |
| —CH₂—CH₂OSO₂CH₃ | H | H | OC₂H₅ | |
| —CH₂—CH₂OSO₂CH₃ | H | H | NH₂ | |
| —CH₂—CH₂OSO₂CH₃ | 5-CF₃ | H | NH₂ | |
| —CH₂—CH₂—CH₂—OH | H | H | CH₃ | |
| —CH₂—CH₂—CH₂—OH | H | H | OC₂H₅ | |
| —CH₂—CH₂—CH₂—OH | H | H | NH₂ | |
| —CH₂—CH₂—OC(O)CH₃ | H | H | NHCH₃ | |
| —CH₂—CH₂—OC(O)CH₃ | H | H | NH₂ | |

TABLE VIII $$\text{R}_2\text{—}\underset{\underset{\text{SO}_2\text{NHCN}}{\overset{\text{OR}_1}{|}}}{\text{C}_6\text{H}_3}\text{—}\underset{\underset{\text{R}_3}{|}}{\overset{\text{O}}{\text{C}}}\text{—}\underset{\text{N}}{\overset{\text{N}}{\diagdown}}\overset{\text{X}}{\underset{\text{Y}}{\diagup}}\text{Z}$$

| R₁ | R₂ | R₃ | X | Y | Z | m.p.(°C.) |
|---|---|---|---|---|---|---|
| —CH₂—CH₂—OH | H | H | CH₃ | C₂H₅ | CH | |
| —CH₂—CH₂—OH | H | H | CH₃ | OC₂H₅ | CH | |
| —CH₂—CH₂—OH | H | H | CH₃ | CH₂OCH₃ | CH | |
| —CH₂—CH₂—OH | H | H | CH₃ | CH(OCH₃)₂ | CH | |
| —CH₂—CH₂—OH | H | H | CH₃ | O—CH₂\CH\O—CH₂ (dioxolane) | CH | |
| —CH₂—CH₂—OH | H | H | CH₃ | NH₂ | CH | |
| —CH₂—CH₂—OH | H | H | CH₃ | NHCH₃ | CH | |
| —CH₂—CH₂—OH | H | H | CH₃ | N(CH₃)₂ | CH | |
| —CH₂—CH₂—OH | H | H | OCH₃ | C₂H₅ | CH | |
| —CH₂—CH₂—OH | H | H | OCH₃ | OC₂H₅ | CH | |
| —CH₂—CH₂—OH | H | H | OCH₃ | CH₂OCH₃ | CH | |
| —CH₂—CH₂—OH | H | H | OCH₃ | CH(OCH₃)₂ | CH | |
| —CH₂—CH₂—OH | H | H | OCH₃ | O—CH₂\CH\O—CH₂ (dioxolane) | CH | |
| —CH₂—CH₂—OH | H | H | OCH₃ | NH₂ | CH | |
| —CH₂—CH₂—OH | H | H | OCH₃ | NHCH₃ | CH | |
| —CH₂—CH₂—OH | H | H | OCH₃ | N(CH₃)₂ | CH | |
| —CH₂—CH₂—OH | H | H | CH₃ | C₂H₅ | N | |
| —CH₂—CH₂—OH | H | H | CH₃ | OC₂H₅ | N | |
| —CH₂—CH₂—OH | H | H | CH₃ | CH₂OCH₃ | N | |
| —CH₂—CH₂—OH | H | H | CH₃ | CH(OCH₃)₂ | N | |
| —CH₂—CH₂—OH | H | H | CH₃ | O—CH₂\CH\O—CH₂ (dioxolane) | N | |
| —CH₂—CH₂—OH | H | H | CH₃ | NH₂ | N | |
| —CH₂—CH₂—OH | H | H | CH₃ | NHCH₃ | N | |
| —CH₂—CH₂—OH | H | H | CH₃ | N(CH₃)₂ | N | |
| —CH₂—CH₂—OH | H | H | OCH₃ | C₂H₅ | N | |
| —CH₂—CH₂—OH | H | H | OCH₃ | OC₂H₅ | N | |
| —CH₂—CH₂—OH | H | H | OCH₃ | CH₂OCH₃ | N | |
| —CH₂—CH₂—OH | H | H | OCH₃ | CH(OCH₃)₂ | N | |
| —CH₂—CH₂—OH | H | H | OCH₃ | O—CH₂\CH\O—CH₂ (dioxolane) | N | |
| —CH₂—CH₂—OH | H | H | OCH₃ | NH₂ | N | |
| —CH₂—CH₂—OH | H | H | OCH₃ | NHCH₃ | N | |
| —CH₂—CH₂—OH | H | H | OCH₃ | N(CH₃)₂ | N | |
| —CH₂—CH₂—CH₂—OH | H | H | CH₃ | OC₂H₅ | CH | |
| —CH₂—CH₂—CH₂—OH | H | H | CH₃ | CH₂OCH₃ | CH | |
| —CH₂—CH₂—CH₂—OH | H | H | CH₃ | CH(OCH₃)₂ | CH | |
| —CH₂—CH₂—CH₂—OH | H | H | CH₃ | O—CH₂\CH\O—CH₂ (dioxolane) | CH | |
| —CH₂—CH₂—CH₂—OH | H | H | CH₃ | NH₂ | CH | |
| —CH₂—CH₂—CH₂—OH | H | H | CH₃ | NHCH₃ | CH | |
| —CH₂—CH₂—CH₂—OH | H | H | CH₃ | N(CH₃)₂ | CH | |
| —CH₂—CH₂—CH₂—OH | H | H | OCH₃ | C₂H₅ | CH | |
| —CH₂—CH₂—CH₂—OH | H | H | OCH₃ | OC₂H₅ | CH | |

TABLE VIII-continued

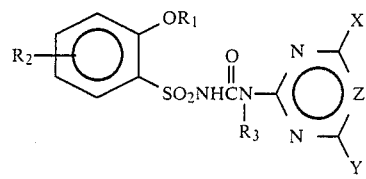

| R₁ | R₂ | R₃ | X | Y | Z | m.p.(°C.) |
|---|---|---|---|---|---|---|
| —CH₂—CH₂—CH₂—OH | H | H | OCH₃ | CH₂OCH₃ | CH | |
| —CH₂—CH₂—CH₂—OH | H | H | OCH₃ | O—CH₂ / CH \ O—CH₂ | CH | |
| —CH₂—CH₂—CH₂—OH | H | H | OCH₃ | NH₂ | CH | |
| —CH₂—CH₂—CH₂—OH | H | H | OCH₃ | NHCH₃ | CH | |
| —CH₂—CH₂—CH₂—OH | H | H | OCH₃ | N(CH₃)₂ | CH | |
| —CH₂—CH₂—CH₂—OH | H | H | CH₃ | OC₂H₅ | N | |
| —CH₂—CH₂—CH₂—OH | H | H | CH₃ | CH₂OCH₃ | N | |
| —CH₂—CH₂—CH₂—OH | H | H | CH₃ | CH(OCH₃)₂ | N | |
| —CH₂—CH₂—CH₂—OH | H | H | CH₃ | NH₂ | N | |
| —CH₂—CH₂—CH₂—OH | H | H | CH₃ | NHCH₃ | N | |
| —CH₂—CH₂—CH₂—OH | H | H | CH₃ | N(CH₃)₂ | N | |
| —CH₂—CH₂—CH₂—OH | H | H | OCH₃ | C₂H₅ | N | |
| —CH₂—CH₂—CH₂—OH | H | H | OCH₃ | OC₂H₅ | N | |
| —CH₂—CH₂—CH₂—OH | H | H | OCH₃ | CH₂OCH₃ | N | |
| —CH₂—CH₂—CH₂—OH | H | H | OCH₃ | CH(OCH₃)₂ | N | |
| —CH₂—CH₂—CH₂—OH | H | H | OCH₃ | O—CH₂ / CH \ O—CH₂ | N | |
| —CH₂—CH₂—CH₂—OH | H | H | OCH₃ | NH₂ | N | |
| —CH₂—CH₂—CH₂—OH | H | H | OCH₃ | NHCH₃ | N | |
| —CH₂—CH₂—CH₂—OH | H | H | OCH₃ | N(CH₃)₂ | N | |
| —CH₂—CH₂—OSO₂CH₃ | H | H | CH₃ | CH(OCH₃)₂ | CH | |
| —CH₂—CH₂—OSO₂CH₃ | H | H | CH₃ | NH₂ | CH | |
| —CH₂—CH₂—OSO₂CH₃ | H | H | CH₃ | N(CH₃)₂ | CH | |
| —CH₂—CH₂—OSO₂CH₃ | H | H | OCH₃ | CH₂OCH₃ | CH | |
| —CH₂—CH₂—OSO₂CH₃ | H | H | OCH₃ | NH₂ | CH | |
| —CH₂—CH₂—OSO₂CH₃ | H | H | CH₃ | CH(OCH₃)₂ | N | |
| —CH₂—CH₂—OSO₂CH₃ | H | H | CH₃ | NH₂ | N | |
| —CH₂—CH₂—OSO₂CH₃ | H | H | OCH₃ | CH₂OCH₃ | N | |
| —CH₂—CH₂—OSO₂CH₃ | H | H | OCH₃ | NHCH₃ | N | |
| —CH₂—CH₂—OC(O)CH₃ | H | H | CH₃ | CH(OCH₃)₂ | CH | |
| —CH₂—CH₂—OC(O)CH₃ | H | H | CH₃ | NH₂ | CN | |
| —CH₂—CH₂—OC(O)CH₃ | H | H | OCH₃ | O—CH₂ / CH \ O—CH₂ | CH | |
| —CH₂—CH₂—OC(O)CH₃ | H | H | OCH₃ | NH₂ | CH | |
| —CH₂—CH₂—OC(O)CH₃ | H | H | CH₃ | CH(OCH₃)₂ | N | |
| —CH₂—CH₂—OC(O)CH₃ | H | H | OCH₃ | NH₂ | N | |
| —CH₂—CH₂—OH | 5-CF₃ | H | CH₃ | NH₂ | CH | |
| —CH₂CH—OH (CH₃) | H | H | OCH₃ | CH(OCH₃)₂ | N | |
| —CH₂—CH₂—CH₂—OH | 5-CF₃ | H | OCH₃ | NH₂ | CH | |
| —CH₂—CH₂—OSO₂CH₃ | 5-CF₃ | H | OCH₃ | O—CH₂ / CH \ O—CH₂ | CH | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE IX

|  | Active Ingredient | Weight Percent* | |
| --- | --- | --- | --- |
|  |  | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annula", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

| Wettable Powder | |
| --- | --- |
| N—[(4-methoxy-6-methyl-1,3,5-triazin-2-yl)aminocarbonyl]-2-(2-hydroxyethoxy)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

| Wettable Powder | |
| --- | --- |
| N—[(4,6-dimethoxy-1,3,5-triazin-2-yl)aminocarbonyl]-2-(2-hydroxyethoxy)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

| Granule | |
| --- | --- |
| Wettable Powder of Example 7 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 9

| Extruded Pellet | |
| --- | --- |
| N—[(4-methoxy-6-methylpyrimidin-2-yl)aminocarbonyl]-2-(2-methylsulfonyloxyethoxy)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

| Oil Suspension | |
|---|---|
| N—[(4,6-dimethoxypyrimidin-2-yl)aminocarbonyl]-2-(2-hydroxyethoxy)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

| Wettable Powder | |
|---|---|
| N—[(4-methoxy-6-methylpyrimidin-2-yl)aminocarbonyl]-2-(2-hydroxyethoxy)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

| Low Strength Granule | |
|---|---|
| N—[(4,6-dimethylpyrimidin-2-yl)aminocarbonyl]-2-(2-hydroxyethoxy)benzenesulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

| Aqueous Suspension | |
|---|---|
| N—[(4,6-dimethoxypyrimidin-2-yl)aminocarbonyl]-2-(2-hydroxyethoxy)benzenesulfonamide, ammonium salt | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

| Solution | |
|---|---|
| N—[(4-methoxy-6-methylpyrimidin-2-yl)aminocarbonyl]-2-(2-hydroxyethoxy)benzenesulfonamide, ammonium salt | 5% |
| water | 95% |

The salt is added directly to the water with stirring to produce the solution, which may then be packaged for use.

EXAMPLE 15

| Low Strength Granule | |
|---|---|
| N—[(4,6-dimethoxy-1,3,5-triazin-2-yl)aminocarbonyl]-2-(2-hydroxyethoxy)benzenesulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

| Granule | |
|---|---|
| N—[(4-methoxy-6-methyl-1,3,5-triazin-2-yl)aminocarbonyl]-2-(2-hydroxyethoxy)benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 17

| High Strength Concentrate | |
|---|---|
| N—[(4-methoxy-6-methylpyrimidin-2-yl)amincarbonyl]-2-(2-methylsulfonyloxyethoxy)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 18

| Wettable Powder | |
| --- | --- |
| N—[(4,6-dimethylpyrimidin-2-yl)aminocarbonyl]-2-(2-hydroxyethoxy)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 19

| Wettable Powder | |
| --- | --- |
| N—[(4-methoxy-6-methylpyrimidin-2-yl)aminocarbonyl]-2-(2-methylsulfonyloxyethoxy)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

| Oil Suspension | |
| --- | --- |
| N—[(4,6-dimethylpyrimidin-2-yl)aminocarbonyl]-2-(2-hydroxyethoxy)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 21

| Dust | |
| --- | --- |
| N—[(4-methoxy-6-methylpyrimidin-2-yl)aminocarbonyl]-2-(2-hydroxyethoxy)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are highly active herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- and/or post-emergence weed control in crops, such as wheat, rice and corn.

The rates of application for the compounds of the invention ae determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.005 to 5 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (*Digitaria* sp.), barnyard-grass (*Echinochloa crusgalli*), wild oats (*Avena fatua*), sicklepod (*Cassia obtusifolia*), morningglory (*Ipomoea* sp.), cocklebur (*Xanthium* sp.), sorghum, corn, soybean, cotton, sugar beet, rice, wheat and purple nutsedge (*Cyperus rotundus*) tubers were planted and treated pre-emergence with the test chemicals dissolved in a non-phytotoxic solvent. At the same time, these crop and weed species, along with bush bean, were treated with a soil/foliage application. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
E=emergence inhibition;
G=growth retardation;
H=formative effects;
U=unusual pigmentation; and
6Y=abscised buds or flowers.

The data indicate that the compounds tested by this procedure possess very high pre- and post-emergence activity. At least one compound, Compound 5, at this early stage of testing exhibits utility for weed control in cereal crops.

COMPOUNDS

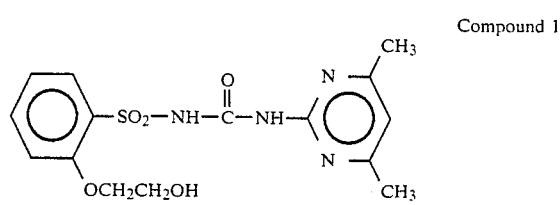

Compound 1

Compound 2
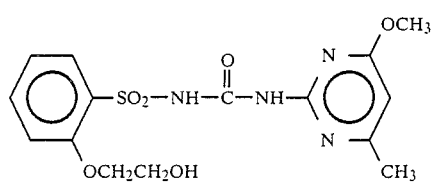

Compound 3
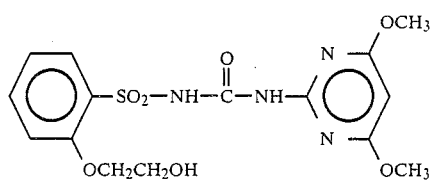

Compound 4
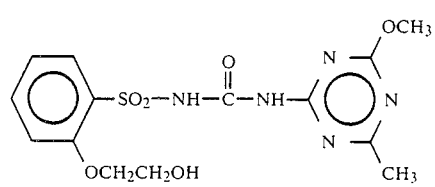

Compound 5
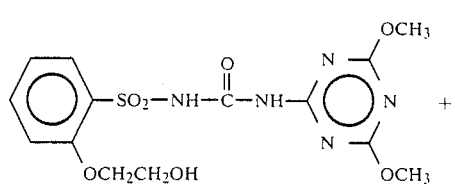

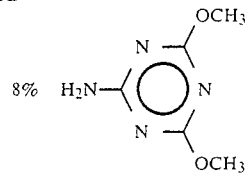
8% H₂N—

Compound 6
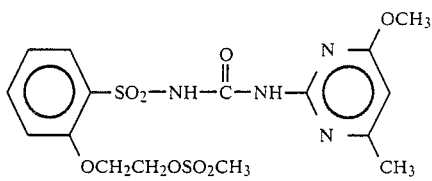

TABLE A

| Rate kg/ha | Cmpd. 1 0.4 | Cmpd. 2 0.4 | Cmpd. 3 0.4 | Cmpd. 4 0.4 | Cmpd. 5 0.4 | Cmpd. 6 .05 |
|---|---|---|---|---|---|---|
| POST-EMERGENCE | | | | | | |
| Bush bean | 5C,9G,6Y | 5C,9G,6Y | 9C | 9C | 6C,9G,6Y | — |
| Cotton | 5C,9G | 9C | 5C,9G | 6C,9G | 5C,9G | 10C |
| Morningglory | 5C,9G | 9C | 5C,9G | 10C | 9C | 3C,8H |
| Cocklebur | 5C,9G | 10C | 10C | 10C | 9C | 3C,9G |
| Sicklepod | 5C,9G | 9C | 6C,9G | 10C | 9C | 3C,6G |
| Nutsedge | 9G | 6C,9G | 10C | 9C | 9C | 2C,8G |
| Crabgrass | 2C,9G | 10C | 3C,9G | 8C | 1C,6G | 2C,5G |
| Barnyardgrass | 6C,9G | 10C | 6C,9G | 9C | 2C,9H | 3C,8H |
| Wild Oats | 2C,9G | 5C,9G | 3C,9H | 6G | 4G | 2C,9G |
| Wheat | 9G | 9C | 3C,9G | 2G | 0 | 8G |
| Corn | 5C,9G | 3C,9G | 2U,9G | 5C,9G | 1U,8H | 3C,9H |
| Soybean | 4C,9G | 5C,9G | 5C,9G | 6C,9G | 6C,9G | 5C,9G |
| Rice | 6C,9G | 6C,9G | 6C,9G | 5C,9G | 2C,8G | 4C,8G |
| Sorghum | 3C,9G | 3C,9G | 4C,9G | 2C,9G | 2C,8H | 4C,8H |
| Sugar beet | 9C | 9C | 9C | 10C | 9C | 3C,8G |
| PRE-EMERGENCE | | | | | | |
| Morningglory | 9G | 9C | 9C | 9C | 9C | 8G |
| Cocklebur | 9H | 9H | 9H | 9H | 9H | 9H |
| Sicklepod | 5C,9G | 9C | 2C,8G | 4C,9G | 5C,9G | 5G |
| Nutsedge | 10E | 10E | 10E | 9G | 9G | 2C,5G |
| Crabgrass | 1C,5G | 2C,8G | 2C,5G | 2C | 1C | 2C,3G |
| Barnyardgrass | 2C,9H | 5C,9H | 5C,9G | 3C,8H | 3C,8H | 3C,9H |
| Wild Oats | 2C,9G | 5C,9H | 9G | 9G | 2C,4G | 3C,9G |
| Wheat | 5C,9H | 10E | 10H | 1C,7G | 2G | 3C,9G |
| Corn | 10E | 10H | 2U,9H | 3C,9G | 9G | 3C,9H |
| Soybean | 8H | 9H | 9H | 9H | 9H | 2C,5H |
| Rice | 10E | 10E | 10E | 10E | 9H | 3C,9H |
| Sorghum | 10H | 10H | 5C,9H | 9H | 2C,8H | 3C,9H |
| Sugar beet | 9C | 10E | 10C | 10E | 10E | 3C,9G |
| Cotton | — | — | — | — | — | 2C,9G |

TEST B

Two 25 cm diameter plastic containers were lined with plastic bags and filled with limed Woodstown sandy loam. A 25 cm diameter Lucite ® planting template was used to slightly compress the soil within each container and to provide indentations for the planting of nine test species. Seeds of the following species were placed in one container: cocklebur (*Xanthium pensylvanicum*), velvetleaf (*Abutilon theophrasti*), sugar beets (*Beta vulgaris*), sicklepod (*Cassia obtusifolia*), morningglory (*Ipomoea hederacea*), teaweed (*Sida spinosa*), cotton (*Gossypium hirsutum*), jimsonweed (*Datura stramonium*) and soybean (*Glycine max.*). The sedcond pot was planted with seeds or tubers of the following species: purple nutsedge (*Cyperus rotundus*), rice (*Oryza sativa*), giant foxtail (*Setaria faberii*), crabgrass (*Digitaria sanguinalis*), johnson-grass (*Sorghum halepense*), wild oats (*Avena fatua*), wheat (*Triticum aestivum*), barnyardgrass (*Echinochloa crusgalli*) and corn (*Zea mays*). Both containers were then topped with an approximately 1 cm layer of soil to cover the seeds. These two containers were then sprayed pre-emergence with several test compounds from within the scope of the invention. Following treatment, the plantings received approximately 1 cm of simulated rainfall in a period of 150 minutes.

Approximately twenty-eight days after treatment, the plants were visually rated for response to the chemical treatment utilizing the rating system described previously for Test A.

cm diameter by 13 cm deep): soybeans, cotton, corn, rice, wheat, sorghum, velvetleaf (*Abutilon theophrasti*), sesbania (*Sesbania exaltata*), Sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*), wild oats (*Avena fatua*) and johnsongrass (*Sorghum halepense*). Sugar beets were grown in soil in a paper cup (12 cm diameter by 13 cm deep). All plants were sprayed approximately 14 days after planting.

Some of the compounds tested by this procedure are useful for the post-emergence control of broadleaved weeds in major crops such as corn, rice and wheat.

TABLE B

PRE-EMERGENCE ON WOODSTOWN SANDY LOAM

| Rate g/ha | Compound 1 | | | | Compound 2 | | | Compound 3 | | | | Compound 4 | | | | Compound 5 | | | |
|---|---|---|---|---|---|---|---|---|---|---|---|---|---|---|---|---|---|---|---|
| | 4 | 15 | 64 | 250 | 4 | 15 | 64 | 4 | 15 | 64 | 250 | 4 | 15 | 64 | 250 | 4 | 15 | 64 | 250 |
| Crabgrass | 0 | 4G | 7G | 9G | 4G | 6G | 9G | 0 | 3G | 5G | 8G | 0 | 2G | 5G | 8G | 0 | 0 | 0 | 0 |
| Barnyardgrass | 0 | 5G | 9G | 9G | 6G | 9G | 9G | 2G | 7G | 9G | 9G | 3G | 4G | 7G | 8G | 0 | 3G | 5G | 6G |
| Wild Oats | 0 | 2G | 3G | 8G | 4G | 7G | 9G | 0 | 5G | 8G | 9G | 0 | 0 | 2G | 3G | 0 | 0 | 0 | 0 |
| Johnsongrass | 4G | 8G | 9G | 9G | 8G | 9G | 9G | 6G | 8G | 9G | 9G | 4G | 7G | 7G | 9G | 0 | 2G | 6G | 6G |
| Giant foxtail | 0 | 4G | 7G | 9G | 7G | 8G | 9G | 5G | 6G | 9G | 9G | 0 | 0 | 3G | 7G | 0 | 2G | 5G | 6G |
| Sugar beets | 0 | 3G | 7G | 9G | 7G | 9G | 10C | 6G | 7G | 10C | 10C | 10C | 10C | 10C | 10C | 9G | 10C | 10C | 10C |
| Corn | 2G | 4G | 7G | 9G | 4G | 5G | 8G | 0 | 2G | 4G | 6G | 0 | 3G | 6G | 7G | 0 | 4G | 4G | 7G |
| Cocklebur | 0 | 3G | 7G | 8G | 5G | 10C | 10C | 8G | 9G | 10C | 10C | 8G | 9G | 9G | 9G | 7G | 9G | 9G | 9G |
| Nutsedge | 0 | 2G | 9G | 10C | 8G | 8G | 9G | 3G | 5G | 8G | 9G | 7G | 7G | 8G | 9G | 7G | 8G | 8G | 9G |
| Cotton | 3G | 2G | 7G | 9G | 7G | 6G | 9G | 2G | 4G | 7G | 9G | 9G | 9G | 9G | 9G | 7G | 9G | 9G | 9G |
| Morningglory | 3G | 5G | 5G | 8G | 8G | 9G | 9G | 0 | 7G | 9G | 9G | 8G | 9G | 9G | 9G | 8G | 9G | 9G | 9G |
| Sicklepod | 4G | 3G | 7G | 9G | 7G | 9G | 9G | 0 | 5G | 8G | 9G | 9G | 9G | 9G | 9G | 7G | 9G | 9G | 9G |
| Teaweed | 3G | 3G | 6G | 9G | 8G | 9G | 9G | 2G | 8G | 9G | 9G | 8G | 9G | 9G | 9G | 7G | 9G | 9G | 9G |
| Velvetleaf | 2G | 6G | 8G | 9G | 9G | 9G | 9G | 3G | 8G | 9G | 9G | 9G | 9G | 9G | 10C | 8G | 9G | 9G | 9G |
| Jimsonweed | 2G | 6G | 8G | 9G | 7G | 8G | 9G | 0 | 7G | 8G | 9G | 9G | 9G | 9G | 10C | 4G | 9G | 9G | 9G |
| Soybean | 0 | 2G | 8G | 9G | 8G | 9G | 9G | 8G | 9G | 9G | 9G | 8G | 9G | 9G | 9G | 4G | 9G | 9G | 9G |
| Rice | 2G | 6G | 9G | 9G | 6G | 8G | 9G | 0 | 4G | 8G | 8G | 5G | 7G | 8G | 9G | 0 | 0 | 6G | 7G |
| Wheat | 0 | 2G | 6G | 9G | 6G | 7G | 9G | 4G | 6G | 7G | 8G | 0 | 2G | 4G | 5G | 0 | 0 | 2G | 2G |

TEST C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25

TABLE C

| | Over-the-Top Soil/Foliage Treatment | | | | | | | | | | | | | | | | |
|---|---|---|---|---|---|---|---|---|---|---|---|---|---|---|---|---|---|
| | Compound 1 | | | | Compound 2 | | | | Compound 3 | | | | Compound 5 | | | | |
| Rate g/ha | 4 | 16 | 64 | 250 | 4 | 16 | 64 | 250 | 4 | 16 | 64 | 250 | 4 | 16 | 64 | 250 |
| Soybeans | 5G | 8C | 10C | 10C | 9G | 10G | 10C | 10C | 10G | 10G | 10G | 10C | 10G | 10G | 10C | 10C |
| Velvetleaf | 0 | 5G | 9G | 10G | 4G | 9G | 9G | 10G | 7G | 9G | 10G | 10G | 6G | 9G | 10C | 10C |
| Sesbania | 6G | 6G | 9G | 10G | 5G | 8G | 9G | 10C | 10G | 10G | 10C | 10G | 10C | 10C | 10C | 10C |
| Sicklepod | 2G | — | 3C | 4G | 2C | 2G | 8C | 8G | 2C | 10G | 8G | 9G | 7G | 8G | 10G | 10G |
| Cotton | 0 | 6C | 9G | 10G | 4C | 10C | 9G | 10G | 3C | 9G | 9G | 9G | 7G | 8G | 10C | 10C |
| Morningglory | 0 | 2G | 6G | 8C | 0 | 6G | 9G | 9G | 6G | 7G | 9G | 9G | 8G | 9G | 10C | 10G |
| Sugar beet | 6G | 3G | 6G | 8G | 5G | 8G | 9G | 8G | 6G | 8G | 10G | 10G | 10G | 10C | 10G | 10G |
| Jimsonweed | 0 | — | 4C | 7G | 4G | 4G | — | 9G | 4C | 6G | 9G | 8G | 5C | — | 9G | 10G |
| Cocklebur | 5G | 6C | 9G | 10G | 5G | 8G | 9G | 8G | — | 6G | 10C | 9G | 10C | 10C | 10C | 10C |
| Corn | 2C | 5G | 7U | 8G | 5G | 7G | 8G | 8G | 1C | 1G | 3G | 5G | 0 | 0 | 1U | 2G |
| Crabgrass | 0 | 0 | 5G | 8G | 0 | 5G | 7G | 7G | 0 | 0 | 3G | 4G | 0 | 0 | 0 | 0 |
| Rice | 3G | 5C | 5C | 5C | 4G | 4G | 4C | 5C | 5G | 5C | 4C | 5C | 4C | 1G | 0 | 0 |
| Nutsedge | 0 | 1G | 5G | 5G | 0 | 7G | 5G | 4G | 7G | 2G | 6G | 4G | 0 | 0 | 0 | 4G |
| Barnyardgrass | 6G | 8G | 8G | 8G | 7G | 8G | 8C | 9C | 7G | 8G | 7G | 8C | 0 | 0 | 5G | 8G |
| Wheat | 0 | 1G | 4G | 5G | 1G | 4G | 7G | 8G | 0 | 4G | 5G | 6G | 0 | 0 | 0 | 0 |
| Giant foxtail | 0 | 0 | 0 | 6G | 0 | 4G | 8G | 8G | 0 | 0 | 2G | 5G | 0 | 0 | 0 | 0 |
| Wild Oats | 0 | 1G | 4G | 7G | 1G | 4G | 7G | 8G | 0 | 0 | 4G | 6G | 0 | 0 | 0 | 0 |
| Sorghum | 6G | 4G | 5G | 5C | 3G | 4G | 4G | 6C | 5G | 5G | 4C | 6U | 0 | 2G | 2G | 4C |
| Johnsongrass | 0 | 5C | 6G | 6G | 3G | 6G | 7G | 7G | 2G | 4G | 5G | 6C | 0 | 0 | 0 | 5G |

TEST D

Two plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium* multiflorum) and rapeseed (Brassica napus). The other pan was planted with seeds of Russian thistle (Salsola kali), cleavers (Galium aparine), speedwell (Veronica persica), kochia (Kochia scoparia), shepherd's purse (Capsella bursa-pastoris), Matricaria inodora, black nightshade (Solanum nigrum), wild buckwheat (Polygonum convolvulus) and sugar beets (Beta vulgaris). The above two pans were treated preemergence. At the same time two pans in which the above plant species were already growing were treated post-emergence. Plant heights at the time of treatment ranged from 1-20 cm depending on plant species.

The test compound was diluted with a non-phytotoxic solvent and sprayed over-the-top of the pans. An untreated control and a solvent alone control were included for comparison. All treatments were maintained in the greenhouse for 19-22 days at which time the treatments were compared to the controls and the effects visually rated. The recorded data are presented in Table D. It will be seen that the compound tested has utility for pre- and/or post-emergence weed control in cereal crops such as wheat and barley.

TABLE D

|  | Compound 5 | | | |
| --- | --- | --- | --- | --- |
|  | Pre-Emergence | | Post-Emergence | |
| Rate g/ha | 16 | 64 | 16 | 64 |
| wheat | 0 | 0 | 0 | 0 |
| barley | 0 | 0 | 0 | 0 |
| wild oats | 0 | 0 | 0 | 0 |
| cheatgrass | 0 | 0 | 0 | 0 |
| blackgrass | 0 | 7G | 0 | 4G |
| annual bluegrass | 0 | 5G | 0 | 0 |
| green foxtail | 0 | 0 | 0 | 0 |
| Italian ryegrass | 0 | 0 | 0 | 0 |
| rapeseed | 9G | 10C | 9G,7C | 10C |
| Matricaria inodora | 8G | 10C | 7G | 8G,7C |
| Galium aparine | 9G | 9G,9C | 8G,7C | 10C |
| Russian thistle | 7G | 7G | 10C | 10C |
| shepherd's purse | 10C | 10C | 10C | 10C |
| kochia | 8G | 10C | 9G | 9G,7C |
| black nightshade | 2G | 4G | 0 | 6G |
| speedwell | 0 | 4G | 0 | 0 |
| wild buckwheat | 7G | 8G,3C | 9G | 10C |
| sugar beets | 8G | 9G | 10C | 10C |

What is claimed is:

1. A compound of the formula:

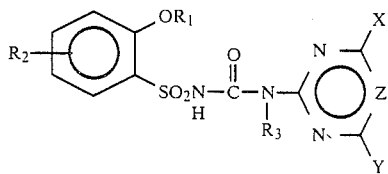

wherein

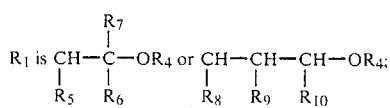

$R_2$ is H, F, Cl, Br, $CH_3$, $OCH_3$ or $CF_3$;
$R_3$ is H or $CH_3$;
$R_4$ is H, $COCH_3$, $COC_2H_5$, $COCH_2CH_2CH_3$, $COCH(CH_3)_2$, $COC_6H_5$, $CONHCH_3$, $CONHC_2H_5$, $CON(CH_3)_2$,

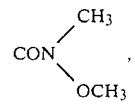

$CONHC_6H_5$, $SO_2CH_3$, $SO_2C_2H_5$, $SO_2C_6H_5$,

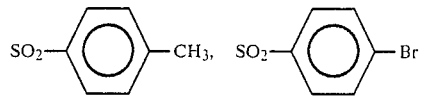

or $SO_2CF_3$;
$R_5$ is H or $CH_3$;
$R_6$ is H or $CH_3$;
$R_7$ is H or $CH_3$;
$R_8$ is H or $CH_3$;
$R_9$ is H or $CH_3$;
$R_{10}$ is H or $CH_3$;
Z is N;
X is $CH_3$ or $OCH_3$; and
Y is $CH_3$, $C_2H_5$, $OCH_3$, $OC_2H_5$, $CH_2OCH_3$, $CH(OCH_3)_2$,

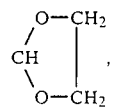

$NH_2$, $NHCH_3$ or $N(CH_3)_2$;
provided that
(1) when $R_6$ and $R_7$ are both $CH_3$, then $R_4$ is H; and
(2) when either $R_8$, $R_9$ or $R_{10}$ is $CH_3$, then the others must be H;
and their agriculturally suitable salts.

2. A compound of claim 1 where

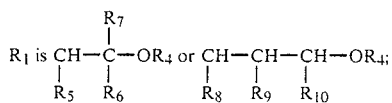

$R_7$ is H;
$R_8$ is H;
$R_9$ is H; and
$R_{10}$ is H.

3. A compound of claim 2 where $R_3$ is H.

4. A compound of claim 3 where $R_2$ is H and $R_4$ is H, $COCH_3$, $CONHCH_3$, $SO_2CH_3$ or $SO_2CF_3$.

5. A compound of claim 4 where

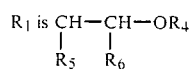

or $CH_2CH_2CH_2OR_4$;
$R_4$ is H;
$R_5$ is H; and
$R_6$ is H.

6. A compound of claim 5 where X and Y are independently $CH_3$ or $OCH_3$.

7. The compound of claim 1 which is N-[(4-methoxy-6-methyl-1,3,5-triazin-2-yl)aminocarbonyl]-2-(2-hydroxyethoxy)benzenesulfonamide.

8. The compound of claim 1 which is N-[(4,6-dimethoxy-1,3,5-triazin-2-yl)aminocarbonyl]-2-(2-hydroxyethoxy)benzenesulfonamide.

9. A composition suitable for controlling the growth of undesired vegetation which comprises an effective amount of a compound of claim 1 and at least one of the following: surfactant, solid or liquid inert diluent.

10. A composition suitable for controlling the growth of undesired vegetation which comprises an effective amount of a compound of claim 2 and at least one of the following: surfactant, solid or liquid inert diluent.

11. A composition suitable for controlling the growth of undesired vegetation which comprises an effective amount of a compound of claim 3 and at least one of the following: surfactant, solid or liquid inert diluent.

12. A composition suitable for controlling the growth of undesired vegetation which comprises an effective amount of a compound of claim 4 and at least one of the following: surfactant, solid or liquid inert diluent.

13. A composition suitable for controlling the growth of undesired vegetation which comprises an effective amount of a compound of claim 5 and at least one of the following: surfactant, solid or liquid inert diluent.

14. A composition suitable for controlling the growth of undesired vegetation which comprises an effective amount of a compound of claim 6 and at least one of the following: surfactant, solid or liquid inert diluent.

15. A composition suitable for controlling the growth of undesired vegetation which comprises an effective amount of the compound of claim 7 and at least one of the following: surfactant, solid or liquid inert diluent.

16. A composition suitable for controlling the growth of undesired vegetation which comprises an effective amount of the compound of claim 8 and at least one of the following: surfactant, solid or liquid inert diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of the compound of claim 7.

24. A method for controlling the growth of undesired vegetation which comprises applying to the locus to be protected an effective amount of the compound of claim 8.

* * * * *